(12) United States Patent
Nam et al.

(10) Patent No.: US 9,644,191 B2
(45) Date of Patent: May 9, 2017

(54) METHOD FOR PRODUCING TRANSGENIC PLANT WITH INCREASE SYRINGIN PRODUCTION AND PLANT PRODUCED BY USING THE SAME

(71) Applicant: DONG-A UNIVERSITY RESEARCH FOUNDATION FOR INDUSTRY-ACADEMY COOPERATION, Busan (KR)

(72) Inventors: Jae Sung Nam, Busan (KR); Tack Min Kwon, Busan (KR); Yang Chu, Busan (KR)

(73) Assignee: DONG-A UNIVERSITY RESEARCH FOUNDATION FOR INDUSTRY-ACADEMY COOPERATION, Busan (KR)

( * ) Notice: Subject to any disclaimer, the term of this patent is extended or adjusted under 35 U.S.C. 154(b) by 143 days.

(21) Appl. No.: 14/435,445

(22) PCT Filed: Dec. 13, 2012

(86) PCT No.: PCT/KR2012/010856
§ 371 (c)(1),
(2) Date: Apr. 13, 2015

(87) PCT Pub. No.: WO2014/058104
PCT Pub. Date: Apr. 17, 2014

(65) Prior Publication Data
US 2015/0252338 A1   Sep. 10, 2015

(30) Foreign Application Priority Data

Oct. 11, 2012  (KR) .................. 10-2012-0112763
Nov. 6, 2012   (KR) .................. 10-2012-0124906

(51) Int. Cl.
*C12N 9/10*    (2006.01)
*C12N 15/82*   (2006.01)

(52) U.S. Cl.
CPC ......... *C12N 9/1051* (2013.01); *C12N 9/1048* (2013.01); *C12N 15/8245* (2013.01)

(58) Field of Classification Search
None
See application file for complete search history.

*Primary Examiner* — Brent Page
(74) *Attorney, Agent, or Firm* — The PL Law Group, PLLC

(57) ABSTRACT

The present invention relates to recombinant glycosyl transferase UGT72E3/2 gene having an excellent syringin synthesis ability based on remarkable enzyme specificity for sinapyl alcohol, a method for producing a transgenic plant with increased syringin production based on a metabolic process which uses F5H and CHS genes that are involved with the phenylpropanoid biosynthesis pathway and Myb58 gene as a transcription factor for positive regulation of the gene that is involved with lignin biosynthesis pathway, and a plant obtained by the method. According to the present invention, syringin with various pharmaceutical applications can be effectively produced in a large amount in a plant, and thus it is expected to allow the development of an industry relating to agrobiological materials that are highly valuable as foods or pharmaceuticals.

20 Claims, 14 Drawing Sheets

Fig. 3
A
B
C

Fig. 6

```
   1 ATGCATATCACAAAACCACACGCCGCCATGTTTTCCAGTCCCGGAATGGGCCATGTCCTC
  61 CCGGTGATCGAGCTAGCTAAGCGTCTCTCCGCTAACCACGGCTTCCACGTCACCGTCTTC
 121 GTCCTTGAAACTGACGCAGCCTCCGTTCAGTCCAAGCTCCTTAACTCAACCGGTGTTGAC
 181 ATCGTCAACCTTCCATCGCCCGACATTTCTGGCTTGGTAGACCCCAACGCCCATGTGGTG
 241 ACCAAGATCGGAGTCATTATGCGTGAAGCTGTTCCAACCCTCCGATCCAAGATCGTTGCC
 301 ATGCATCAAAACCCAACGGCTCTGATCATTGACTTGTTTGGCACAGATGCGTTATGTCTT
 361 GCAGCGGAGTTAAACATGTTGACTTATGTCTTTATCGCTTCCAACGCGCGTTATCTCGGA
 421 GTTTCGATATATTATCCAACTTTGGACGAAGTTATCAAAGAAGAGCACACAGTGCAACGA
 481 AAACCGCTCACTATACCGGGGTGTGAACCGGTTAGATTTGAAGATATTATGGATGCATAT
 541 CTGGTTCCGGACGAACCGGTGTACCACGATTTGGTTCGTCACTGTCTGGCCTACCCAAAA
 601 GCGGATGGAATCTTGGTGAATACATGGGAAGAGATGGAGCCCAAATCATTAAAGTCCCTT
 661 CAAGACCCGAAACTTTTGGGCCGGGTCGCTCGTGTACCGGTTTATCCGGTTGGTCCGTTA
 721 TGCAGACCGATACAATCATCCACGACCGATCACCCGGTTTTTGATTGGTTAAACAAACAA
 781 CCAAACGAGTCGGTTCTCTACATTTCCTTCGGGAGTGGTGGTTCTCTAACGGCTCAACAG
 841 TTAACCGAATTGGCGTGGGGGCTCGAGGAGAGCCAGCAACGGTTTATATGGGTGGTTCGA
 901 CCGCCCGTTGACGGCTCGTCTTGCAGTGATTATTTCTCGGCTAAAGGCGGTGTAACCAAA
 961 GACAACACGCCAGAGTATCTACCAGAAGGGTTCGTGACTCGTACTTGCGATAGAGGTTTC
1021 GTGGTCCCCTCATGGGCCCCACAAGCTGAAATCCTGTCCCATCGGGCCGTTGGTGGGTTT
1081 TTGACCCATTGCGGTTGGAGCTCGACGTTGGAAAGCGTCGTTGGCGGCGTTCCGATGATC
1141 GCATGGCCACTTTTTGCCGAGCAGAATATGAATGCGGCGTTGCTCAGCGACGAACTGGGA
1201 ATCGCAGTCAGATTGGATGATCCAAAGGAGGATATTTCTAGGTGGAAGATTGAGGCGTTG
1261 GTGAGGAAGGTTATGACTGAGAAGGAAGGTGAAGCGATGAGAAGGAAAGTGAAGAAGTTG
1321 AGAGACTCGGCGGAGATGTCACTGAGCATTGACGGTGGTGGTTTGGCGCACGAGTCGCTT
1381 TGCAGAGTCACCAAGGAGTGTCAACGGTTTTTGGAACGTGTCGTGGACTTGTCACGTGGT
1441 GCTTAG
```

```
   1 M H I T K P H A A M F S S P G M G H V L
  21 P V I E L A K R L S A N H G F H V T V F
  41 V L E T D A A S V Q S K L L N S T G V D
  61 I V N L P S P D I S G L V D P N A H V V
  81 T K I G V I M R E A V P T L R S K I V A
 101 M H Q N P T A L I I D L F G T D A L C L
 121 A A E L N M L T Y V F I A S N A R Y L G
 141 V S I Y Y P T L D E V I K E E H T V Q R
 161 K P L T I P G C E P V R F E D I M D A Y
 181 L V P D E P V Y H D L V R H C L A Y P K
 201 A D G I L V N T W E M E P K S L K S L
 221 Q D P K L L G R V A R V P V Y P V G P L
 241 C R P I Q S S T D H P V F D W L N K Q
 261 P N E S V L Y I S F G S G G S L T A Q Q
 281 L T E L A W G L E E S Q Q R F I W V V R
 301 P P V D G S S C S D Y F S A K G V T K
 321 D N T P E Y L P E G F V T R T C D R G F
 341 V V P S W A P Q A E I L S H R A V G G F
 361 L T H C G W S S T L E S V V G G V P M I
 381 A W P L F A E Q N M N A A L L S D E L G
 401 I A V R L D D P K E D I S R W K I E A L
 421 V R K V M T E K E G E A M R R K V K K L
 441 R D S A E M S L S I D G G G L A H E S L
 461 C R V T K E C Q R F L E R V V D L S R G
 481 A
```

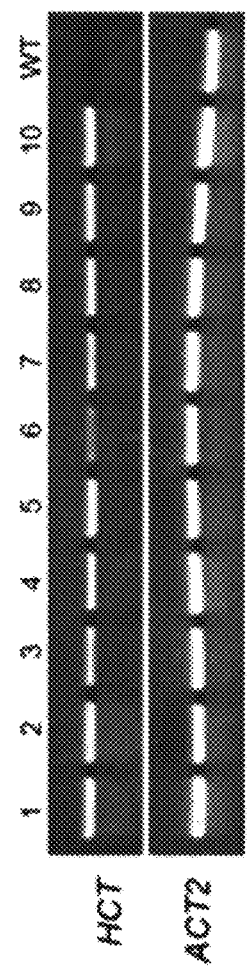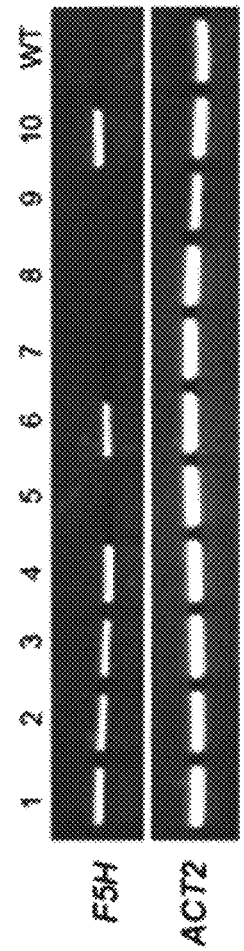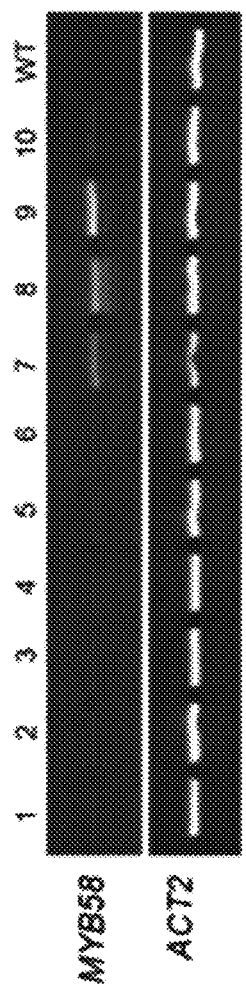
Fig. 9

SEQUENCE LISTING

```
<160> NUMBER OF SEQ ID NOS: 17

<210> SEQ ID NO 1
<211> LENGTH: 1446
<212> TYPE: DNA
<213> ORGANISM: Artificial Sequence
<220> FEATURE:
<223> OTHER INFORMATION: UGT72E3/2 recombinant gene

<400> SEQUENCE: 1
atgcatatca caaaaccaca cgccgccatg ttttccagtc ccggaatggg ccatgtcctc      60
ccggtgatcg agctagctaa gcgtctctcc gctaaccacg gcttccacgt caccgtcttc     120
gtccttgaaa ctgacgcagc ctccgttcag tccaagctcc ttaactcaac cggtgttgac     180
atcgtcaacc ttccatcgcc cgacatttct ggcttggtag accccaacgc ccatgtggtg     240
accaagatcg gagtcattat gcgtgaagct gttccaaccc tccgatccaa gatcgttgcc     300
atgcatcaaa acccaacggc tctgatcatt gacttgtttg gcacagatgc gttatgtctt     360
```

```
gcagcggagt taaacatgtt gacttatgtc tttatcgctt ccaacgcgcg ttatctcgga      420
gtttcgatat attatccaac tttggacgaa gttatcaaag aagagcacac agtgcaacga      480
aaaccgctca ctataccggg gtgtgaaccg gttagatttg aagatattat ggatgcatat      540
ctggttccgg acgaaccggt gtaccacgat ttggttcgtc actgtctggc ctacccaaaa      600
gcggatggaa tcttggtgaa tacatgggaa gagatggagc ccaaatcatt aaagtccctt      660
caagacccga aacttttggg ccgggtcgct cgtgtaccgg tttatccggt tggtccgtta      720
tgcagaccga taatcatc cacgaccgat cacccggttt ttgattggtt aaacaaacaa      780
ccaaacgagt cggttctcta catttccttc gggagtggtg gttctctaac ggctcaacag      840
ttaaccgaat tggcgtgggg gctcgaggag agccagcaac ggtttatatg ggtggttcga      900
ccgcccgttg acggctcgtc ttgcagtgat tatttctcgg ctaaaggcgg tgtaaccaaa      960
gacaacacgc cagagtatct accagaaggg ttcgtgactc gtacttgcga tagaggtttc     1020
gtggtcccct catgggcccc acaagctgaa atcctgtccc atcgggccgt tggtgggttt     1080
ttgacccatt gcggttggag ctcgacgttg gaaagcgtcg ttggcggcgt tccgatgatc     1140
gcatggccac tttttgccga gcagaatatg aatgcggcgt tgctcagcga cgaactggga     1200
atcgcagtca gattggatga tccaaaggag gatatttcta ggtggaagat tgaggcgttg     1260
gtgaggaagg ttatgactga gaaggaaggt gaagcgatga aaggaaagt gaagaagttg     1320
agagactcgg cggagatgtc actgagcatt gacggtggtg gtttggcgca cgagtcgctt     1380
tgcagagtca ccaaggagtg tcaacggttt ttggaacgtg tcgtggactt gtcacgtggt     1440
gcttag                                                                1446
```

<210> SEQ ID NO 2
<211> LENGTH: 481
<212> TYPE: PRT
<213> ORGANISM: Artificial Sequence
<220> FEATURE:
<223> OTHER INFORMATION: UGT72E3/2 recombinant protein

<400> SEQUENCE: 2

```
Met His Ile Thr Lys Pro His Ala Ala Met Phe Ser Ser Pro Gly Met
1               5                   10                  15

Gly His Val Leu Pro Val Ile Glu Leu Ala Lys Arg Leu Ser Ala Asn
            20                  25                  30

His Gly Phe His Val Thr Val Phe Val Leu Glu Thr Asp Ala Ala Ser
        35                  40                  45

Val Gln Ser Lys Leu Leu Asn Ser Thr Gly Val Asp Ile Val Asn Leu
    50                  55                  60

Pro Ser Pro Asp Ile Ser Gly Leu Val Asp Pro Asn Ala His Val Val
65                  70                  75                  80

Thr Lys Ile Gly Val Ile Met Arg Glu Ala Val Pro Thr Leu Arg Ser
                85                  90                  95

Lys Ile Val Ala Met His Gln Asn Pro Thr Ala Leu Ile Ile Asp Leu
            100                 105                 110

Phe Gly Thr Asp Ala Leu Cys Leu Ala Ala Glu Leu Asn Met Leu Thr
        115                 120                 125

Tyr Val Phe Ile Ala Ser Asn Ala Arg Tyr Leu Gly Val Ser Ile Tyr
    130                 135                 140

Tyr Pro Thr Leu Asp Glu Val Ile Lys Glu His Thr Val Gln Arg
145                 150                 155                 160

Lys Pro Leu Thr Ile Pro Gly Cys Glu Pro Val Arg Phe Glu Asp Ile
```

```
                        165                 170                 175
Met Asp Ala Tyr Leu Val Pro Asp Glu Pro Val Tyr His Asp Leu Val
                180                 185                 190

Arg His Cys Leu Ala Tyr Pro Lys Ala Asp Gly Ile Leu Val Asn Thr
            195                 200                 205

Trp Glu Glu Met Glu Pro Lys Ser Leu Lys Ser Leu Gln Asp Pro Lys
        210                 215                 220

Leu Leu Gly Arg Val Ala Arg Val Pro Val Tyr Pro Val Gly Pro Leu
225                 230                 235                 240

Cys Arg Pro Ile Gln Ser Ser Thr Thr Asp His Pro Val Phe Asp Trp
                245                 250                 255

Leu Asn Lys Gln Pro Asn Glu Ser Val Leu Tyr Ile Ser Phe Gly Ser
            260                 265                 270

Gly Gly Ser Leu Thr Ala Gln Gln Leu Thr Glu Leu Ala Trp Gly Leu
        275                 280                 285

Glu Glu Ser Gln Gln Arg Phe Ile Trp Val Val Arg Pro Pro Val Asp
290                 295                 300

Gly Ser Ser Cys Ser Asp Tyr Phe Ser Ala Lys Gly Gly Val Thr Lys
305                 310                 315                 320

Asp Asn Thr Pro Glu Tyr Leu Pro Glu Gly Phe Val Thr Arg Thr Cys
                325                 330                 335

Asp Arg Gly Phe Val Val Pro Ser Trp Ala Pro Gln Ala Glu Ile Leu
            340                 345                 350

Ser His Arg Ala Val Gly Gly Phe Leu Thr His Cys Gly Trp Ser Ser
        355                 360                 365

Thr Leu Glu Ser Val Val Gly Val Pro Met Ile Ala Trp Pro Leu
        370                 375                 380

Phe Ala Glu Gln Asn Met Asn Ala Ala Leu Leu Ser Asp Glu Leu Gly
385                 390                 395                 400

Ile Ala Val Arg Leu Asp Asp Pro Lys Glu Asp Ile Ser Arg Trp Lys
                405                 410                 415

Ile Glu Ala Leu Val Arg Lys Val Met Thr Glu Lys Glu Gly Glu Ala
            420                 425                 430

Met Arg Arg Lys Val Lys Lys Leu Arg Asp Ser Ala Glu Met Ser Leu
        435                 440                 445

Ser Ile Asp Gly Gly Leu Ala His Glu Ser Leu Cys Arg Val Thr
        450                 455                 460

Lys Glu Cys Gln Arg Phe Leu Glu Arg Val Val Asp Leu Ser Arg Gly
465                 470                 475                 480

Ala

<210> SEQ ID NO 3
<211> LENGTH: 1563
<212> TYPE: DNA
<213> ORGANISM: Arabidopsis thaliana

<400> SEQUENCE: 3
atggagtctt ctatatcaca aacactaagc aaactatcag atcccacgac gtctcttgtc     60
atcgttgtct ctcttttcat cttcatcagc ttcatcacac ggcggcgaag gcctccatat    120
cctcccggtc acgaggttg gcccatcata ggcaacatgt taatgatgga ccaactcacc    180
caccgtggtt tagccaattt agctaaaaag tatggcggat gtgccatct ccgcatggga    240 ttcctccata tgtacgctgt ctcatcaccc gaggtggctc gacaagtcct tcaagtccaa    300
```

```
gacagcgtct tctcgaaccg gcctgcaact atagctataa gctatctgac ttacgaccga      360
gcggacatgg ctttcgctca ctacggaccg ttttggagac agatgagaaa agtgtgtgtc      420
atgaaggtgt ttagccgtaa aagagctgag tcatgggctt cagttcgtga tgaagtggac      480
aaaatggtcc ggtcggtctc ttgtaacgtt ggtaagccta taaacgtcgg ggagcaaatt      540
tttgcactga cccgcaacat aacttaccgg gcagcgtttg ggtcagcctg cgagaaggga      600
caagacgagt tcataagaat cttacaagag ttctctaagc tttttggagc cttcaacgta      660
gcggatttca taccatattt cgggtggatc gatccgcaag ggataaacaa gcggctcgtg      720
aaggcccgta atgatctaga cggatttatt gacgatatta tcgatgaaca tatgaagaag      780
aaggagaatc aaaacgctgt ggatgatggg gatgttgtcg ataccgatat ggttgatgat      840
cttcttgctt tttacagtga agaggccaaa ttagtcagtg agacagcgga tcttcaaaat      900
tccatcaaac ttacccgtga caatatcaaa gcaatcatca tggacgttat gtttggagga      960
acggaaacgg tagcgtcggc gatagagtgg gccttaacgg agttattacg gagccccgag     1020
gatctaaaac gggtccaaca agaactcgcc gaagtcgttg gacttgacag acgagttgaa     1080
gaatccgaca tcgagaagtt gacttatctc aaatgcacac tcaaagaaac cctaaggatg     1140
cacccaccga tccctctcct cctccacgaa accgcggagg acactagtat cgacggtttc     1200
ttcattccca agaaatctcg tgtgatgatc aacgcgtttg ccataggacg cgacccaacc     1260
tcttggactg acccggacac gtttagacca tcgaggtttt tggaaccggg cgtaccggat     1320
ttcaaaggga gcaatttcga gtttataccg ttcgggtcgg gtcgtagatc gtgcccgggt     1380
atgcaactag ggttatacgc gcttgactta gccgtggctc atatattaca ttgcttcacg     1440
tggaaattac ctgatgggat gaaaccaagt gagctcgaca tgaatgatgt gtttggtctc     1500
acggctccta agccacgcg gcttttcgcc gtgccaacca cgcgcctcat ctgtgctctt     1560
taa                                                                   1563

<210> SEQ ID NO 4
<211> LENGTH: 520
<212> TYPE: PRT
<213> ORGANISM: Arabidopsis thaliana

<400> SEQUENCE: 4

Met Glu Ser Ser Ile Ser Gln Thr Leu Ser Lys Leu Ser Asp Pro Thr
1               5                   10                  15

Thr Ser Leu Val Ile Val Val Ser Leu Phe Ile Phe Ile Ser Phe Ile
            20                  25                  30

Thr Arg Arg Arg Arg Pro Pro Tyr Pro Pro Gly Pro Arg Gly Trp Pro
        35                  40                  45

Ile Ile Gly Asn Met Leu Met Met Asp Gln Leu Thr His Arg Gly Leu
    50                  55                  60

Ala Asn Leu Ala Lys Lys Tyr Gly Gly Leu Cys His Leu Arg Met Gly
65                  70                  75                  80

Phe Leu His Met Tyr Ala Val Ser Ser Pro Glu Val Ala Arg Gln Val
                85                  90                  95

Leu Gln Val Gln Asp Ser Val Phe Ser Asn Arg Pro Ala Thr Ile Ala
            100                 105                 110

Ile Ser Tyr Leu Thr Tyr Asp Arg Ala Asp Met Ala Phe Ala His Tyr
        115                 120                 125

Gly Pro Phe Trp Arg Gln Met Arg Lys Val Cys Val Met Lys Val Phe
    130                 135                 140
```

-continued

Ser Arg Lys Arg Ala Glu Ser Trp Ala Ser Val Arg Asp Glu Val Asp
145                 150                 155                 160

Lys Met Val Arg Ser Val Ser Cys Asn Val Gly Lys Pro Ile Asn Val
                165                 170                 175

Gly Glu Gln Ile Phe Ala Leu Thr Arg Asn Ile Thr Tyr Arg Ala Ala
            180                 185                 190

Phe Gly Ser Ala Cys Glu Lys Gly Gln Asp Glu Phe Ile Arg Ile Leu
        195                 200                 205

Gln Glu Phe Ser Lys Leu Phe Gly Ala Phe Asn Val Ala Asp Phe Ile
210                 215                 220

Pro Tyr Phe Gly Trp Ile Asp Pro Gln Gly Ile Asn Lys Arg Leu Val
225                 230                 235                 240

Lys Ala Arg Asn Asp Leu Asp Gly Phe Ile Asp Ile Ile Asp Glu
                245                 250                 255

His Met Lys Lys Lys Glu Asn Gln Asn Ala Val Asp Asp Gly Asp Val
            260                 265                 270

Val Asp Thr Asp Met Val Asp Leu Leu Ala Phe Tyr Ser Glu Glu
        275                 280                 285

Ala Lys Leu Val Ser Glu Thr Ala Asp Leu Gln Asn Ser Ile Lys Leu
290                 295                 300

Thr Arg Asp Asn Ile Lys Ala Ile Ile Met Asp Val Met Phe Gly Gly
305                 310                 315                 320

Thr Glu Thr Val Ala Ser Ile Glu Trp Ala Leu Thr Glu Leu Leu
                325                 330                 335

Arg Ser Pro Glu Asp Leu Lys Arg Val Gln Gln Glu Leu Ala Glu Val
            340                 345                 350

Val Gly Leu Asp Arg Arg Val Glu Glu Ser Asp Ile Glu Lys Leu Thr
        355                 360                 365

Tyr Leu Lys Cys Thr Leu Lys Glu Thr Leu Arg Met His Pro Pro Ile
370                 375                 380

Pro Leu Leu Leu His Glu Thr Ala Glu Asp Thr Ser Ile Asp Gly Phe
385                 390                 395                 400

Phe Ile Pro Lys Lys Ser Arg Val Met Ile Asn Ala Phe Ala Ile Gly
                405                 410                 415

Arg Asp Pro Thr Ser Trp Thr Asp Pro Asp Thr Phe Arg Pro Ser Arg
            420                 425                 430

Phe Leu Glu Pro Gly Val Pro Asp Phe Lys Gly Ser Asn Phe Glu Phe
        435                 440                 445

Ile Pro Phe Gly Ser Gly Arg Arg Ser Cys Pro Gly Met Gln Leu Gly
450                 455                 460

Leu Tyr Ala Leu Asp Leu Ala Val Ala His Ile Leu His Cys Phe Thr
465                 470                 475                 480

Trp Lys Leu Pro Asp Gly Met Lys Pro Ser Glu Leu Asp Met Asn Asp
                485                 490                 495

Val Phe Gly Leu Thr Ala Pro Lys Ala Thr Arg Leu Phe Ala Val Pro
            500                 505                 510

Thr Thr Arg Leu Ile Cys Ala Leu
        515                 520

<210> SEQ ID NO 5
<211> LENGTH: 825
<212> TYPE: DNA
<213> ORGANISM: Arabidopsis thaliana

<400> SEQUENCE: 5

```
atgggcaaag gaagagcacc atgttgtgac aaaaccaaag tgaagagagg accatggagc    60
catgatgaag acttgaaact catctctttc attcacaaga atggtcatga aattggaga    120
tctctcccaa agcaagctgg attgttgagg tgtggcaaga gttgtcgtct gcgatggatt   180
aattacctca gacctgatgt gaaacgtggc aatttcagtg cagaggaaga agacaccatc   240
atcaaacttc accagagctt tggtaacaag tggtcgaaga ttgcttctaa gctgcctgga   300
agaacagaca tgagatcaa gaatgtgtgg catacacatc tcaagaaaag attgagctcg    360
gaaactaacc ttaatgccga tgaagcgggt tcaaaaggtt ctttgaatga agaagagaac   420
tctcaagagt catctccaaa tgcttcaatg tcttttgctg gttccaacat ttcaagcaaa   480
gacgatgatg cacagataag tcaaatgttt gagcacattc taacttatag cgagtttacg   540
gggatgttac aagaggtaga caaaccagag ctgctggaga tgccttttga tttagatcct   600
gacatttgga gtttcataga tggttcagac tcattccaac aaccagagaa cagagctctt   660
caagagtctg aagaagatga agttgataaa tggtttaagc acctggaaag cgaactcggg   720
ttagaagaaa acgataacca acaacaacaa caacagcata aacagggaac agaagatgaa   780
cattcatcat cactcttgga gagttacgag ctcctcatac attaa                   825
```

<210> SEQ ID NO 6
<211> LENGTH: 274
<212> TYPE: PRT
<213> ORGANISM: Arabidopsis thaliana

<400> SEQUENCE: 6

```
Met Gly Lys Gly Arg Ala Pro Cys Cys Asp Lys Thr Lys Val Lys Arg
1               5                   10                  15

Gly Pro Trp Ser His Asp Glu Asp Leu Lys Leu Ile Ser Phe Ile His
            20                  25                  30

Lys Asn Gly His Glu Asn Trp Arg Ser Leu Pro Lys Gln Ala Gly Leu
        35                  40                  45

Leu Arg Cys Gly Lys Ser Cys Arg Leu Arg Trp Ile Asn Tyr Leu Arg
    50                  55                  60

Pro Asp Val Lys Arg Gly Asn Phe Ser Ala Glu Glu Asp Thr Ile
65                  70                  75                  80

Ile Lys Leu His Gln Ser Phe Gly Asn Lys Trp Ser Lys Ile Ala Ser
                85                  90                  95

Lys Leu Pro Gly Arg Thr Asp Asn Glu Ile Lys Asn Val Trp His Thr
            100                 105                 110

His Leu Lys Lys Arg Leu Ser Ser Glu Thr Asn Leu Asn Ala Asp Glu
        115                 120                 125

Ala Gly Ser Lys Gly Ser Leu Asn Glu Glu Asn Ser Gln Glu Ser
    130                 135                 140

Ser Pro Asn Ala Ser Met Ser Phe Ala Gly Ser Asn Ile Ser Ser Lys
145                 150                 155                 160

Asp Asp Asp Ala Gln Ile Ser Gln Met Phe Glu His Ile Leu Thr Tyr
                165                 170                 175

Ser Glu Phe Thr Gly Met Leu Gln Glu Val Asp Lys Pro Glu Leu Leu
            180                 185                 190

Glu Met Pro Phe Asp Leu Asp Pro Asp Ile Trp Ser Phe Ile Asp Gly
        195                 200                 205

Ser Asp Ser Phe Gln Gln Pro Glu Asn Arg Ala Leu Gln Glu Ser Glu
    210                 215                 220
```

```
Glu Asp Glu Val Asp Lys Trp Phe Lys His Leu Glu Ser Glu Leu Gly
225                 230                 235                 240

Leu Glu Glu Asn Asp Asn Gln Gln Gln Gln Gln His Lys Gln Gly
            245                 250                 255

Thr Glu Asp Glu His Ser Ser Ser Leu Leu Glu Ser Tyr Glu Leu Leu
        260                 265                 270

Ile His

<210> SEQ ID NO 7
<211> LENGTH: 885
<212> TYPE: DNA
<213> ORGANISM: Arabidopsis thaliana

<400> SEQUENCE: 7
atggggaagg gaagagcacc ttgttgtgac aagaccaaag tgaagagagg tccatggagc      60
ccagaagaag acattaaact catctctttc attcaaaagt ttggtcatga gaactggaga     120
tctctcccca acaatctgg gctattgagg tgtgggaaga gttgtcgtct aaggtggatt      180
aactatctta ggccagatct gaagcgtggc aacttcactt cagaggagga gaaacaatc     240 attaagcttc accacaacta tgggaacaag tggtcgaaaa tcgcttctca acttccaggt    300
agaacagata cgagatcaa gaatgtgtgg cacactcatc taaagaaaag actggctcag    360
agctcaggaa ctgcagatga accggcctcg ccttgttcga gtgattctgt ttctcgtggg    420
aaagatgata agtcatctca cgtagaagat tctttgaaca gagagactaa tcataggaat    480
gagttgtcta catctatgtc ttctgggggt tccaaccaac aagatgatcc aaagatagac    540
gaactcaggt ttgagtatat agaagaagct tatagcgagt ttaacgacat tattattcaa    600
gaggtagaca aacccgatct gctggagata ccatttgatt cagatcctga catttggagt    660
ttcttagata cttcaaactc atttcaacaa tccactgcaa atgagaacag ctcaggctca    720
agagcaacaa cagaagaaga gtctgatgag gatgaggtta agaaatggtt caagcaccta    780
gaaagcgaac tcgggttaga agaagacgat aatcaacaac aatacaaaga agaagaatca    840
tcatcatcat cactcttgaa gaactacgag ctcatgatac attga                    885

<210> SEQ ID NO 8
<211> LENGTH: 294
<212> TYPE: PRT
<213> ORGANISM: Arabidopsis thaliana

<400> SEQUENCE: 8

Met Gly Lys Gly Arg Ala Pro Cys Cys Asp Lys Thr Lys Val Lys Arg
1               5                   10                  15

Gly Pro Trp Ser Pro Glu Glu Asp Ile Lys Leu Ile Ser Phe Ile Gln
            20                  25                  30

Lys Phe Gly His Glu Asn Trp Arg Ser Leu Pro Lys Gln Ser Gly Leu
        35                  40                  45

Leu Arg Cys Gly Lys Ser Cys Arg Leu Arg Trp Ile Asn Tyr Leu Arg
    50                  55                  60

Pro Asp Leu Lys Arg Gly Asn Phe Thr Ser Glu Glu Glu Thr Ile
65                  70                  75                  80

Ile Lys Leu His His Asn Tyr Gly Asn Lys Trp Ser Lys Ile Ala Ser
                85                  90                  95

Gln Leu Pro Gly Arg Thr Asp Asn Glu Ile Lys Asn Val Trp His Thr
            100                 105                 110

His Leu Lys Lys Arg Leu Ala Gln Ser Ser Gly Thr Ala Asp Glu Pro
```

|  |  |  | 115 |  |  |  | 120 |  |  |  | 125 |  |  |
|---|---|---|---|---|---|---|---|---|---|---|---|---|---|
Ala | Ser | Pro | Cys | Ser | Ser | Asp | Ser | Val | Ser | Arg | Gly | Lys | Asp | Lys
| | | 130 | | | | | 135 | | | | | 140 | |

Ser Ser His Val Glu Asp Ser Leu Asn Arg Glu Thr Asn His Arg Asn
145                 150                 155                 160

Glu Leu Ser Thr Ser Met Ser Ser Gly Gly Ser Asn Gln Gln Asp Asp
                165                 170                 175

Pro Lys Ile Asp Glu Leu Arg Phe Glu Tyr Ile Glu Glu Ala Tyr Ser
            180                 185                 190

Glu Phe Asn Asp Ile Ile Ile Gln Glu Val Asp Lys Pro Asp Leu Leu
        195                 200                 205

Glu Ile Pro Phe Asp Ser Asp Pro Asp Ile Trp Ser Phe Leu Asp Thr
    210                 215                 220

Ser Asn Ser Phe Gln Gln Ser Thr Ala Asn Glu Asn Ser Ser Gly Ser
225                 230                 235                 240

Arg Ala Thr Thr Glu Glu Glu Ser Asp Glu Asp Glu Val Lys Lys Trp
                245                 250                 255

Phe Lys His Leu Glu Ser Glu Leu Gly Leu Glu Glu Asp Asp Asn Gln
            260                 265                 270

Gln Gln Tyr Lys Glu Glu Glu Ser Ser Ser Ser Ser Leu Leu Lys Asn
        275                 280                 285

Tyr Glu Leu Met Ile His
    290

<210> SEQ ID NO 9
<211> LENGTH: 1188
<212> TYPE: DNA
<213> ORGANISM: Arabidopsis thaliana

<400> SEQUENCE: 9

```
atggtgatgg ctggtgcttc ttctttggat gagatcagac aggctcagag agctgatgga      60
cctgcaggca tcttggctat ggcactgct aaccctgaga accatgtgct tcaggcggag      120
tatcctgact actacttccg catcaccaac agtgaacaca tgaccgacct caaggagaag     180
ttcaagcgca tgtgcgacaa gtcgacaatt cggaaacgtc acatgcatct gacgaggaa      240
ttcctcaagg aaaacccaca catgtgtgct tacatggctc cttctctgga caccagacag     300
gacatcgtgg tggtcgaagt ccctaagcta ggcaaagaag cggcagtgaa ggccatcaag     360
gagtggggcc agcccaagtc aaagatcact catgtcgtct tctgcactac ctccggcgtc     420
gacatgcctg tgctgactac cagctcacc aagcttcttg gtctccgtcc ttccgtcaag      480
cgtctcatga tgtaccagca aggttgcttc gccggcggta ctgtcctccg tatcgctaag     540
gatctcgccg agaacaatcg tggagcacgt gtcctcgttg tctgctctga atcacagcc      600
gttaccttcc gtggtccctc tgacacccac cttgactccc tcgtcggtca ggctcttttc     660
agtgatggcg ccgccgcact cattgtgggg tcggaccctg acacatctgt cggagagaaa     720
cccatctttg agatggtgtc tgccgctcag accatccttc agactctga tggtgccata      780
gacggacatt tgagggaagt tggtctcacc ttccatctcc tcaaggatgt tcccggcctc     840
atctccaaga acattgtgaa gagtctagac gaagcgttta aacctttggg ataagtgac      900
tggaactccc tcttctggat agcccaccct ggaggtccag cgatcctaga ccaggtggag     960
ataaagctag gactaaagga agagaagatg agggcgacac gtcacgtgtt gagcgagtat    1020
ggaaacatgt cgagcgcgtg cgttctcttc atactagacg agatgaggag gaagtcagct    1080
```

```
aaggatggtg tggccacgac aggagaaggg ttggagtggg gtgtcttgtt tggtttcgga   1140
ccaggtctca ctgttgagac agtcgtcttg cacagcgttc ctctctaa              1188
```

<210> SEQ ID NO 10
<211> LENGTH: 395
<212> TYPE: PRT
<213> ORGANISM: Arabidopsis thaliana

<400> SEQUENCE: 10

```
Met Val Met Ala Gly Ala Ser Ser Leu Asp Glu Ile Arg Gln Ala Gln
1               5                   10                  15

Arg Ala Asp Gly Pro Ala Gly Ile Leu Ala Ile Gly Thr Ala Asn Pro
            20                  25                  30

Glu Asn His Val Leu Gln Ala Glu Tyr Pro Asp Tyr Tyr Phe Arg Ile
        35                  40                  45

Thr Asn Ser Glu His Met Thr Asp Leu Lys Glu Lys Phe Lys Arg Met
    50                  55                  60

Cys Asp Lys Ser Thr Ile Arg Lys Arg His Met His Leu Thr Glu Glu
65                  70                  75                  80

Phe Leu Lys Glu Asn Pro His Met Cys Ala Tyr Met Ala Pro Ser Leu
                85                  90                  95

Asp Thr Arg Gln Asp Ile Val Val Glu Val Pro Lys Leu Gly Lys
            100                 105                 110

Glu Ala Ala Val Lys Ala Ile Lys Glu Trp Gly Gln Pro Lys Ser Lys
        115                 120                 125

Ile Thr His Val Val Phe Cys Thr Thr Ser Gly Val Asp Met Pro Gly
    130                 135                 140

Ala Asp Tyr Gln Leu Thr Lys Leu Leu Gly Leu Arg Pro Ser Val Lys
145                 150                 155                 160

Arg Leu Met Met Tyr Gln Gln Gly Cys Phe Ala Gly Gly Thr Val Leu
                165                 170                 175

Arg Ile Ala Lys Asp Leu Ala Glu Asn Asn Arg Gly Ala Arg Val Leu
            180                 185                 190

Val Val Cys Ser Glu Ile Thr Ala Val Thr Phe Arg Gly Pro Ser Asp
        195                 200                 205

Thr His Leu Asp Ser Leu Val Gly Gln Ala Leu Phe Ser Asp Gly Ala
    210                 215                 220

Ala Ala Leu Ile Val Gly Ser Asp Pro Asp Thr Ser Val Gly Glu Lys
225                 230                 235                 240

Pro Ile Phe Glu Met Val Ser Ala Ala Gln Thr Ile Leu Pro Asp Ser
                245                 250                 255

Asp Gly Ala Ile Asp Gly His Leu Arg Glu Val Gly Leu Thr Phe His
            260                 265                 270

Leu Leu Lys Asp Val Pro Gly Leu Ile Ser Lys Asn Ile Val Lys Ser
        275                 280                 285

Leu Asp Glu Ala Phe Lys Pro Leu Gly Ile Ser Asp Trp Asn Ser Leu
    290                 295                 300

Phe Trp Ile Ala His Pro Gly Gly Pro Ala Ile Leu Asp Gln Val Glu
305                 310                 315                 320

Ile Lys Leu Gly Leu Lys Glu Lys Met Arg Ala Thr Arg His Val
                325                 330                 335

Leu Ser Glu Tyr Gly Asn Met Ser Ser Ala Cys Val Leu Phe Ile Leu
            340                 345                 350

Asp Glu Met Arg Arg Lys Ser Ala Lys Asp Gly Val Ala Thr Thr Gly
```

```
                355                 360                 365
Glu Gly Leu Glu Trp Gly Val Leu Phe Gly Phe Gly Pro Gly Leu Thr
    370                 375                 380
Val Glu Thr Val Val Leu His Ser Val Pro Leu
385                 390                 395

<210> SEQ ID NO 11
<211> LENGTH: 1302
<212> TYPE: DNA
<213> ORGANISM: Arabidopsis thaliana

<400> SEQUENCE: 11
atgaaaatta acatcagaga ttccaccatg gtccggcctg ccaccgagac accaatcact     60
aatctttgga actccaacgt cgaccttgtc atccccagat ccatacccc tagtgtctac    120 ttctacagac ccaccggcgc ttccaatttc tttgaccctc aggtcatgaa ggaagctctt    180
tccaaagccc ttgtcccttt ttaccctatg gctggtcgct tgaagagaga cgatgatggt    240
cgtattgaga tcgattgtaa cggtgctggt gttctcttcg ttgtggctga tactccttct    300
gttatcgatg attttggtga ttttgctcct acccttaatc tccgtcagct tattcccgaa    360
gttgatcact ccgctggcat tcactctttc ccgcttctcg ttttgcaggt gactttcttt    420
aaatgtgggg gagcttcact gggggttggg atgcaacatc acgcggcaga tggtttctct    480
ggtcttcatt ttatcaacac atggtctgat atggctcgtg tcttgaccct aaccattcca    540
cctttcattg atcgaacact cctccgagct agggacccgc acagcctgc ttttcatcat    600 gttgaatatc agcctgcacc aagtatgaag atacctcttg atccgtctaa atcaggacct    660
gagaatacca ctgtctctat attcaaatta acacgagacc agcttgttgc tcttaaggcg    720
aaatccaagg aggatgggaa cactgtcagc tacagctcat acgagatgtt ggcagggcat    780
gtgtggagat cagtgggaaa ggcgcgaggg cttccaaacg accaagagac gaaactgtac    840
attgcaactg atggaaggtc tagactacgt ccgcagctgc ctcctggtta ctttgggaat    900
gtgatattca ctgcaacacc attggctgtt gcagggggatt tgttatctaa gccaacatgg    960
tatgctgcag acagattca tgattcttg gttcgtatgg atgataacta tctgaggtca   1020
gctcttgact acctggagat gcagcctgat ctgtcagccc ttgtccgcgg tgcacatacc   1080
tacaagtgcc caaatttggg aatcacaagc tgggttagat acctatttta tgatgcagac   1140
tttggttggg gtcgtcctat ctttatggga cctggtggaa ttccatacga gggtttgtct   1200
tttgtgctac caagtcctac taatgatggc agcttatccg ttgccattgc cctccaatct   1260
gaacacatga aactgtttga aagttttg tttgagatat ga                       1302

<210> SEQ ID NO 12
<211> LENGTH: 433
<212> TYPE: PRT
<213> ORGANISM: Arabidopsis thaliana

<400> SEQUENCE: 12

Met Lys Ile Asn Ile Arg Asp Ser Thr Met Val Arg Pro Ala Thr Glu
1               5                   10                  15

Thr Pro Ile Thr Asn Leu Trp Asn Ser Asn Val Asp Leu Val Ile Pro
            20                  25                  30

Arg Phe His Thr Pro Ser Val Tyr Phe Tyr Arg Pro Thr Gly Ala Ser
        35                  40                  45

Asn Phe Phe Asp Pro Gln Val Met Lys Glu Ala Leu Ser Lys Ala Leu
    50                  55                  60
```

```
Val Pro Phe Tyr Pro Met Ala Gly Arg Leu Lys Arg Asp Asp Gly
 65                  70                  75                  80

Arg Ile Glu Ile Asp Cys Asn Gly Ala Gly Val Leu Phe Val Ala
                 85                  90                  95

Asp Thr Pro Ser Val Ile Asp Asp Phe Gly Asp Phe Ala Pro Thr Leu
            100                 105                 110

Asn Leu Arg Gln Leu Ile Pro Glu Val Asp His Ser Ala Gly Ile His
            115                 120                 125

Ser Phe Pro Leu Leu Val Leu Gln Val Thr Phe Phe Lys Cys Gly Gly
130                 135                 140

Ala Ser Leu Gly Val Gly Met Gln His His Ala Ala Asp Gly Phe Ser
145                 150                 155                 160

Gly Leu His Phe Ile Asn Thr Trp Ser Asp Met Ala Arg Gly Leu Asp
                165                 170                 175

Leu Thr Ile Pro Pro Phe Ile Asp Arg Thr Leu Leu Arg Ala Arg Asp
            180                 185                 190

Pro Pro Gln Pro Ala Phe His His Val Glu Tyr Gln Pro Ala Pro Ser
            195                 200                 205

Met Lys Ile Pro Leu Asp Pro Ser Lys Ser Gly Pro Glu Asn Thr Thr
210                 215                 220

Val Ser Ile Phe Lys Leu Thr Arg Asp Gln Leu Val Ala Leu Lys Ala
225                 230                 235                 240

Lys Ser Lys Glu Asp Gly Asn Thr Val Ser Tyr Ser Ser Tyr Glu Met
                245                 250                 255

Leu Ala Gly His Val Trp Arg Ser Val Gly Lys Ala Arg Gly Leu Pro
                260                 265                 270

Asn Asp Gln Glu Thr Lys Leu Tyr Ile Ala Thr Asp Gly Arg Ser Arg
            275                 280                 285

Leu Arg Pro Gln Leu Pro Pro Gly Tyr Phe Gly Asn Val Ile Phe Thr
290                 295                 300

Ala Thr Pro Leu Ala Val Ala Gly Asp Leu Leu Ser Lys Pro Thr Trp
305                 310                 315                 320

Tyr Ala Ala Gly Gln Ile His Asp Phe Leu Val Arg Met Asp Asp Asn
                325                 330                 335

Tyr Leu Arg Ser Ala Leu Asp Tyr Leu Glu Met Gln Pro Asp Leu Ser
            340                 345                 350

Ala Leu Val Arg Gly Ala His Thr Tyr Lys Cys Pro Asn Leu Gly Ile
            355                 360                 365

Thr Ser Trp Val Arg Leu Pro Ile Tyr Asp Ala Asp Phe Gly Trp Gly
370                 375                 380

Arg Pro Ile Phe Met Gly Pro Gly Gly Ile Pro Tyr Glu Gly Leu Ser
385                 390                 395                 400

Phe Val Leu Pro Ser Pro Thr Asn Asp Gly Ser Leu Ser Val Ala Ile
                405                 410                 415

Ala Leu Gln Ser Glu His Met Lys Leu Phe Glu Lys Phe Leu Phe Glu
            420                 425                 430

Ile
```

<210> SEQ ID NO 13
<211> LENGTH: 27
<212> TYPE: DNA
<213> ORGANISM: Artificial Sequence
<220> FEATURE:
<223> OTHER INFORMATION: primer

```
<400> SEQUENCE: 13
ggttggagct cgacgttgga aagcgtc                                            27

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
ttaaagcagg gcatgcctgc                                                    20

<210> SEQ ID NO 15
<211> LENGTH: 28
<212> TYPE: DNA
<213> ORGANISM: Artificial Sequence
<220> FEATURE:
<223> OTHER INFORMATION: primer

<400> SEQUENCE: 15
ctggttactt tgggaatgtg atattcac                                           28

<210> SEQ ID NO 16
<211> LENGTH: 28
<212> TYPE: DNA
<213> ORGANISM: Artificial Sequence
<220> FEATURE:
<223> OTHER INFORMATION: primer

<400> SEQUENCE: 16
cagacgagtt gaagaatccg acatcgag                                           28

<210> SEQ ID NO 17
<211> LENGTH: 28
<212> TYPE: DNA
<213> ORGANISM: Artificial Sequence
<220> FEATURE:
<223> OTHER INFORMATION: primer

<400> SEQUENCE: 17
cagacgagtt gaagaatccg acatcgag                                           28
```

METHOD FOR PRODUCING TRANSGENIC PLANT WITH INCREASE SYRINGIN PRODUCTION AND PLANT PRODUCED BY USING THE SAME

CROSS REFERENCE TO RELATED APPLICATIONS AND CLAIM OF PRIORITY

This patent application claims benefit under 35 U.S.C. 119(e), 120, 121, or 365(c), and is a National Stage entry from International Application No. PCT/KR2012/010856, filed Dec. 13, 2012, which claims priority to Korean Patent Application Nos. 10-2012-0112763, filed Oct. 11, 2012, and 10-2012-0124906, filed Nov. 6, 2012, the entire contents of which are incorporated herein by reference.

TECHNICAL FIELD

The present invention relates to recombinant glycosyl transferase UGT72E3/2 gene having excellent syringin synthesis activity based on remarkable enzyme specificity for sinapyl alcohol, a method for producing a transgenic plant with increased syringin production based on metabolic engineering with F5H, HCT and CHS genes that are involved with the phenylpropanoid biosynthesis pathway and Myb58 gene as a transcription factor for positive regulation of the genes that are involved with lignin biosynthesis pathway, and a plant obtained by the method.

BACKGROUND ART

From sinapyl alcohol (s type monolignol) as a lignin-constituting component that is generated via phenylpropanoid synthesis pathway, syringin as s type monolignol glycoside is produced by glycosyl transferase (UDP-glucose transferase). In *Arabidopsis thaliana* as a model plant, there are about 100 kinds of glycosyl transferase, and it has been reported that, by forming glycosides of various compounds including plant hormones and secondary metabolites, they regulate the cellular activity and the storage of those compounds in a vacuole. Among them, UGT72E2 and UGT72E3 are reported as a glycosyl transferase responsible for converting firstly monolignol such as coniferyl alcohol and sinapyl alcohol specifically into monolignol-glycosides. Particularly, UGT72E3 as a sinapyl alcohol-specific glycosyl transferase required for syringin production has excellent substrate specificity for sinapyl alcohol, but its glycosyl transferase activity is so low that its application has been very limited. As such, development of a new glycosyl transferase useful for efficient production of syringin in a plant has been remained as a problem to be solved first before mass production and application of syringin, which is a pharmaceutically functional secondary metabolite.

Furthermore, for effective production of syringin in a plant via the phenylpropanoid synthesis pathway, it is also required to have a metabolic engineering technique which increase the content of sinapyl alcohol as a precursor of syringin that is present in a trace amount in a plant cell, as well as a strong glycosyl transferase activity having substrate specificity for sinapyl alcohol.

In particular, eleutheroside B (syringin) is classified as a representative adaptogen derived from plants, which is a pharmaceutical component from *E. senticosus* having excellent efficacy of psychological and physical adaptation against stress. The adaptogen is a terminology indicating a plant secondary metabolite which enhances non-specific resistance of a living body in response to various stresses without causing a side effect. Recently, syringin isolated in the pure state is reported to exhibit an excellent effect for diabetes and depression that become a serious problems of people living in modern-day cities, and thus its application is now broadened more than ever. However, because the area of cultivating *E. senticosus* is limited and there is a huge variation in pharmaceutical components depending on the area of cultivation, it is difficult to have the stable supply of *E. senticosus* required for production of syringin for commercial use. As such, development of a technique for stable production of a plant secondary metabolite like syringin, which is a highly valuable product, based on regulation of plant metabolic pathways using bioengineering techniques is needed.

Meanwhile, in Korean Patent Application Publication No. 2004-0004764, "Composition comprising extract of *E. senticosus* having hepato-protective activity or butyl alcohol soluble fraction thereof and butyl alcohol fraction of syringin and syringaresinol-di-O-β-D-glucopyranoside derivatives having anti-oxidant and hepato-protective activity" is disclosed. Further, in Korean Patent Application Publication No. 1998-0072707, "Pharmaceutical composition of syringin having liver function protecting activity" is disclosed. However, the method for producing a transgenic plant with increased syringin production and a plant obtained therefrom that are disclosed by the present invention have never been described before.

SUMMARY

The present invention is devised in view of the aforementioned needs, and to produce a new recombinant glycosyl transferase having enhanced glycosyl transfer activity while maintaining the substrate specificity at a high level. The recombinant gene UGT72E2/3 and UGT72E3/2 are produced by a domain swapping of UGT72E2 and UGT72E3 genes. Transgenic *Arabidopsis thaliana* over-expressing each of UGT72E family are generated with floral dipping method. Further, as a result of quantitative analysis of the efficiency for syringin synthesis, it is confirmed the newly produced recombinant glycosyl transferase UGT72E3/2 exhibits a significantly increased syringin synthesis than the wild type UGT72E2 and UGT72E3.

Further, in order to increase the syringin production via regulation of the metabolic pathway of a plant, each of the *Arabidopsis thaliana* transgenic plants over-expressing F5H and HCT genes, which regulate an important step for regulating the flow of substrates in the phenylpropanoid synthesis pathway, the transgenic plant deficient of CHS gene function, and the transgenic plant over-expressing Myb58 as a positive regulation transcription factor of the lignin synthesis pathway was produced. As a result of quantitative analysis of the efficiency for syringin synthesis after cross-breeding the aforementioned transgenic plants with the transgenic plant which over-expresses the recombinant glycosyl transferase UGT72E3/2, it was found that, from the newly produced transgenic plant which over-expresses simultaneously the proteins of UGT72E3/2, F5H, and Myb58, the production amount of syringin is increased by 10 times or more compared to the case in which only the UGT72E3/2 protein is over-expressed, and the present invention is completed accordingly.

To solve the problems described above, the present invention provides the recombinant glycosyl transferase UGT72E3/2 protein consisting of the amino acid sequence of SEQ ID NO: 2.

The present invention further provides the gene encoding the UGT72E3/2 protein.

The present invention further provides a recombinant vector comprising the gene encoding the UGT72E3/2 protein.

The present invention further provides a host cell transformed with the recombinant vector.

The present invention further provides a method of increasing syringin synthesis in a plant compared to the wild type, comprising transforming a plant cell with the recombinant vector to over-express the UGT72E3/2 gene.

The present invention further provides a transgenic plant with increased syringin production compared to the wild type, in which the plant is transformed with a recombinant vector comprising the gene encoding the recombinant glycosyl transferase UGT72E3/2 protein.

The present invention further provides a transgenic plant with increased syringin production compared to the wild type, in which the plant is transformed with a recombinant vector comprising the gene encoding the recombinant glycosyl transferase UGT72E3/2 protein and a recombinant vector comprising the gene encoding the F5H (furulate 5-hydroxylase) protein.

The present invention further provides a transgenic plant with increased syringin production compared to the wild type, in which the plant is transformed with a recombinant vector comprising the gene encoding the recombinant glycosyl transferase UGT72E3/2 protein, a recombinant vector comprising the gene encoding the F5H (furulate 5-hydroxylase) protein, and a recombinant vector comprising the gene encoding the Myb58 or Myb63 protein.

The present invention further provides a transgenic plant with increased syringin production in a plant compared to the wild type, in which the plant is transformed with a recombinant vector comprising the gene encoding the recombinant glycosyl transferase UGT72E3/2 protein and a recombinant vector knock-outing the gene encoding the CHS (chalcone synthase) protein.

The present invention further provides a method for producing a transgenic plant with increased syringin production compared to the wild type, in which the plant is transformed with a recombinant vector comprising the gene encoding the UGT72E3/2 protein.

The present invention further provides a method for producing a transgenic plant with increased syringin production compared to the wild type, comprising cross-breeding a transgenic plant which over-expresses the UGT72E3/2 protein and a transgenic plant which over-expresses the F5H protein and selecting a transgenic plant which over-expresses simultaneously the UGT72E3/2 protein and F5H protein.

The present invention further provides a method for producing a transgenic plant with increased syringin production compared to the wild type, comprising cross-breeding a transgenic plant which over-expresses simultaneously the UGT72E3/2 protein and F5H protein and a transgenic plant which over-expresses the Myb58 or Myb63 protein and selecting a transgenic plant which over-expresses simultaneously the UGT72E3/2 protein, F5H protein, and Myb58 or Myb63 protein.

The present invention further provides a method for producing a transgenic plant with increased syringin production compared to the wild type, comprising cross-breeding a transgenic plant which over-expresses the UGT72E3/2 protein and a plant in which the gene encoding the CHS protein is knocked out and selecting a transgenic plant which over-expresses the UGT72E3/2 but has inhibited expression of the CHS protein.

The present invention further provides a transgenic plant with increased syringin production compared to the wild type, which is produced by each method described above, and a seed thereof.

The present invention still further provides a composition for increasing syringin synthesis in a plant comprising, as an effective component, a recombinant vector comprising the gene consisting of the nucleotide sequence of SEQ ID NO: 1 which encodes the UGT72E3/2 protein.

According to the present invention, a new method for efficient and mass production of syringin in various plants, which is derived from a plant and has a widening application as it is reported to exhibit an excellent effect for treating diabetes and depression which become serious problems of people living in modern-day cities, is provided, by which pharmaceutically very useful syringin having a synergistic effect based on sufficient production of sinapyl alcohol, that is a precursor of syringin, and enhancement of the glycosyl transfer activity using the recombinant glycosyl transferase UGT72E3/2 using metabolic engineering via regulation of the gene encoding the recombinant glycosyl transferase UGT72E3/2 protein and the F5H, CHS and Myb58 gene involved with phenylpropanoid synthesis pathway in a plant can be produced efficiently in large scale in various plants. Accordingly, it is expected to allow the development of an industry relating to agrobiological materials that are highly valuable as foods or pharmaceuticals.

BRIEF DESCRIPTION OF THE DRAWINGS

FIG. 3 is a drawing illustrating (A) the recombinant vector used for production of the transformant of the present invention, (B) expression level of the gene transferred in the transformant, and (C) reactivity in the transformed leaves against ultraviolet rays.

FIG. 6 is a drawing illustrating the nucleotide sequence and amino acid sequence of the recombinant glycosyl transferase UGT72E3/2.

FIG. 9 illustrates the result of determining the expression amount of each gene in the *Arabidopsis thaliana*, which over-expresses each of the HCT, F5H and Myb58, based on RT-PCR. As a control group, Actin 2 gene was used.

DETAILED DESCRIPTION

Figure 1:
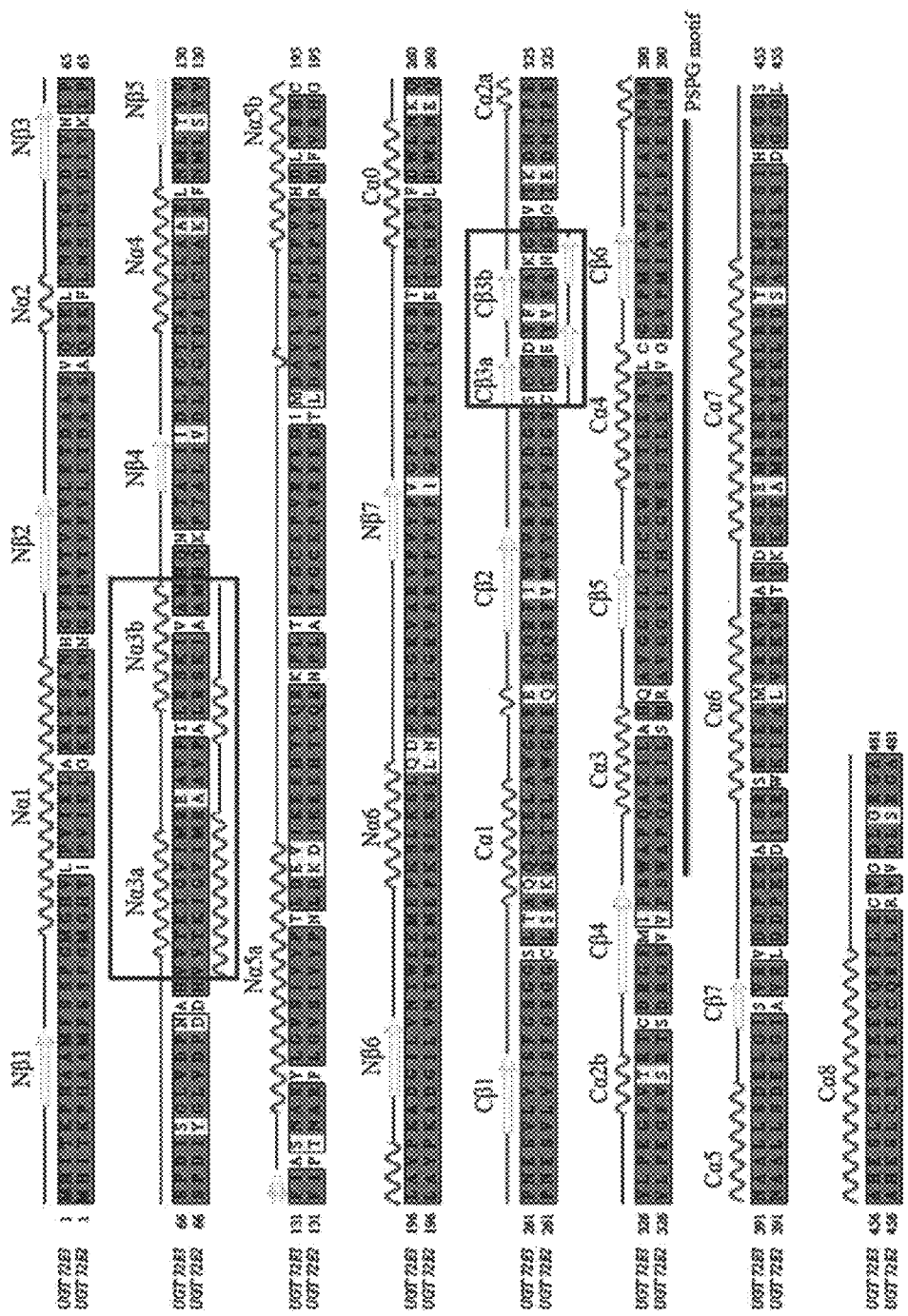
FIG. 1 is a drawing illustrating the comparison of the primary and secondary structures of *Arabidopsis thaliana* glycosyl transferase UGT72E2 and UGT72E3.

In order to achieve the object described above, the present invention provides the recombinant glycosyl transferase UGT72E3/2 protein which consists of an amino acid sequence of SEQ ID NO: 2.

Within the scope of the recombinant glycosyl transferase UGT72E3/2 protein of the present invention, a protein having an amino acid sequence represented by SEQ ID NO: 2 and functional equivalents of the protein are included. The term "functional equivalent" indicates a protein having, as a result of addition, substitution, or deletion of an amino acid, at least 70%, preferably at least 80%, more preferably at least 90%, and even more preferably at least 95% sequence homology with the amino acid sequence represented by SEQ ID NO: 2, and it exhibits substantially the same physiological activity as the protein represented by SEQ ID NO: 2. The term "substantially the same physiological activity" means an increase in syringin synthesis.

The present invention also includes a "fragment", a "derivative", and an "analogue" of the recombinant glycosyl transferase UGT72E3/2 protein. The terms "fragment", "derivative", and "analogue" that are used herein indicate a polypeptide having substantially the same biological function or activity as the recombinant glycosyl transferase UGT72E3/2 polypeptide of the present invention. The derivative and analogue of the present invention can be any one of the followings: (1) a polypeptide in which one or more conservative or non-conservative amino acid residue (preferably, a conservative amino acid residue) is substituted (the substituted amino acid may be either coded or not coded by genetic code), (2) a polypeptide having a substituent (s) on one or more amino acid, (3) a polypeptide derived from a mature polypeptide which is bonded to other compound (i.e., a compound capable of increasing the half life of a polypeptide; for example, polyethylene glycol), and (4) a polypeptide derived from aforementioned polypeptide which is bonded to an additional amino acid sequence (for example, a leading sequence, a secretory sequence, a sequence used for purification of the polypeptide, a proteinogen sequence or fusion protein). The fragment, derivative, and analogue defined herein are well known to a person skilled in the art.

The polynucleotide encoding the mature polypeptide represented by SEQ ID NO: 2 encompasses a coding sequence which encodes the mature polypeptide only; a sequence encoding the mature polypeptide and various additional coding sequences, and; a sequence encoding the mature polypeptide (and any additional coding sequence) and a non-coding sequence.

The term a "polynucleotide encoding a polypeptide" means a polynucleotide which encodes a polypeptide or a polynucleotide further comprising a coding and/or a non-coding sequence.

The present invention also relates to a polynucleotide variant which encodes the same amino acid sequence as the sequence described in the present invention, or a polypeptide containing its fragment, analogue, or derivative. The polynucleotide variant can be either a naturally occurring allele variant or a non-naturally occurring variant. The nucleotide variant encompasses a substitution variant, a deletion variant, and an insertion variant. As it is well known in the pertinent art, the allele variant is an alternative of a polynucleotide, and it may contain one or more substitution, deletion, or insertion of polynucleotide. However, no substantial functional change is yielded in the polynucleotide encoded by the variant.

The present invention also provides a gene encoding the recombinant glycosyl transferase UGT72E3/2 protein.

The gene encoding the recombinant glycosyl transferase UGT72E3/2 protein of the present invention is prepared from UGT72E3 and UGT72E2 genes originating from *Arabidopsis thaliana* by using a domain swapping method.

In the present invention, for having increased syringin production rate, the recombinant genes UGT72E2/3 and UGT72E3/2 were prepared from UGT72E2 and UGT72E3 genes by using a domain swapping method to produce a new recombinant glycosyl transferase having a high glycosyl transferase activity like UGT72E2 while maintaining the substrate specificity for sinapyl alcohol like UGT72E3.

First, the enzyme characteristics of the glycosyl transferase UGT72E clade which has been reported to have a capability of transferring a sugar to sinapyl alcohol, i.e., a precursor of syringin, or structurally similar coniferyl alcohol were determined for about 100 glycosyl transferases from *Arabidopsis thaliana*. The UGT72E clade also has structural characteristics that are similar to a common glycosyl transferase, and it has been reported that the amino terminal domain has a substrate recognition site, the carboxy terminal domain has an enzymatically activated region for transferring a sugar activated by UDP to a substrate, and the PSPG (Plant Secondary Product Glucosyl transferase) at the carboxyl terminal is particularly important for the activity of glycosyl transferase derived from a plant. The UGT72E clade includes glycosyl transferase UGT72E1, UGT72E2, and UGT72E3 having similar nucleotides.

In the present invention, each of the UGT72E2 and UGT72E3 was divided into an amino fragment including the amino acids from number 1 to number 344 and a carboxy fragment including the amino acids from number 345 to number 481. The amino fragment includes a region for determining the substrate recognition specificity and the carboxy terminal includes the PSPG motif, which is important for glycosyl transferase activity. For efficient production of syringin in a plant, the substrate specificity is more important than the glycosyl transferase activity. Thus, instead of having a precise half-cut, a large amino fragment is prepared to include ¾ of the entire length while the carboxy fragment is prepared as a small fragment including PSPG motif. As a result, the recombinant UGT72E3/2 gene of the present invention was produced by linking an amino fragment including the amino acids from number 1 at the amino terminal to number 344 of UGT72E3 to a carboxy fragment including the amino acids from number 345 to number 481 at the carboxy terminal of UGT72E2.

The gene of the present invention can be either a DNA or an RNA which encodes the recombinant glycosyl transferase UGT72E3/2 protein. cDNA, genomic DNA, and an artificial synthetic DNA are included in DNA. DNA can be either single stranded or double-stranded. DNA can be either a coding sequence or a non-coding sequence.

Preferably, the gene of the present invention may contain the nucleotide sequence of SEQ ID NO: 1. Further, homologues of the nucleotide sequence are also within the scope of the present invention. Specifically, the above described gene may comprise a nucleotide sequence which has preferably at least 70%, more preferably at least 80%, still more preferably at least 90%, and most preferably at least 95% homology with the nucleotide sequence of SEQ ID NO: 1.

The "sequence homology %" for a certain polynucleotide is identified by comparing a comparative region with two sequences that are optimally aligned. In this regard, a part of the polynucleotide in comparative region may comprise an addition or a deletion (i.e., a gap) compared to a reference sequence (without any addition or deletion) relative to the optimized alignment of the two sequences.

The present invention also relates to a polynucleotide which hybridizes to a sequence having sequence homology of at least 50%, preferably at least 70%, and more preferably at least 80% with the nucleotide sequence of SEQ ID NO: 1 described above. The present invention particularly relates to a polynucleotide which hybridizes to the polynucleotide of the present invention under a stringent condition. As described herein, the "stringent condition" means (1) hybridization and washing at low ionic strength and high temperature like 0.2×SSC, 0.1% SDS, 60° C.; (2) hybridization in the presence of a denaturing agent like 50% (v/v) formamide, 0.1% bovine serum/0.1% Ficoll, and 42° C., or (3) hybridization occurring between only two sequences having homology of at least 80%, preferably at least 90%, and more preferably at least 95%. Further, the biological function and activity of the polypeptide encoded by a hybridizable nucleotide are the same as those of the mature polypeptide represented by SEQ ID NO: 2.

The present invention also provides a recombinant vector comprising the gene which encodes the aforementioned recombinant glycosyl transferase UGT72E3/2 protein.

The term "recombinant" indicates a cell which replicates a heterogeneous nucleotide or expresses said nucleotide, or a peptide, a heterogeneous peptide, or a protein encoded by a heterogeneous nucleotide. Recombinant cell can express a gene or a gene fragment in the form of a sense or antisense, which are not found in natural state of cell. In addition, a recombinant cell can express a gene that is found in natural state, provided that said gene is modified and re-introduced into the cell by an artificial means.

The recombinant plant expression vector of the present invention can be used as a transient expression vector which allows transient expression of a foreign gene in a plant and also as a plant expression vector which allows permanent expression of a foreign gene in a plant.

A binary vector which can be used for the present invention can be any binary vector comprising RB (right border) and LB (left border) of T-DNA which can transform a plant when it is present with Ti plasmid of *A. tumefaciens*. Preferably, pBI101 (Cat#: 6018-1, Clontech, USA), pBIN19 (Genbank Deposit No. U09365), pBI121, pCAMBIA and the like, which are often used by a skilled person in the pertinent art, are used.

The term "vector" is used herein to refer DNA fragment(s) and nucleotide molecules that are delivered to a cell. Vector can replicate DNA and be independently reproduced in a host cell. The terms "delivery system" and "vector" are often interchangeably used. The term "expression vector" means a recombinant DNA molecule comprising a desired coding sequence and other appropriate nucleotide sequences that are essential for the expression of the operably-linked coding sequence in a specific host organism. The promoter, enhancer, termination signal and polyadenylation signal which can be used in eukaryotic cells are well known in the art.

A preferred example of plant expression vector is Ti-plasmid vector which can transfer a part of itself, i.e., so called T-region, to a plant cell when the vector is present in an appropriate host such as *Agrobacterium tumefaciens*. Other types of Ti-plasmid vector (see, EP 0 116 718 B1) are currently used for transferring a hybrid gene to protoplasts that can produce a new plant by appropriately inserting a plant cell or hybrid DNA to a genome of a plant. Especially preferred form of Ti-plasmid vector is a so-called binary vector which has been disclosed in EP 0 120 516 B1 and U.S. Pat. No. 4,940,838. Other vector that can be used for introducing the gene of the present invention to a host plant can be selected from a double-stranded plant virus (e.g., CaMV), a single-stranded plant virus, and a viral vector which can be originated from Gemini virus, etc., for example a non-complete plant viral vector. Use of said vector can be advantageous especially when a plant host cannot be appropriately transformed.

Expression vector may comprise at least one selective marker. Said selective marker is a nucleotide sequence having a property that can make a target gene get selected by a common chemical method. Examples include all genes that are useful for distinguishing transformed cells from non-transformed cells. Specific examples include a gene resistant to herbicide such as glyphosate and phosphinotricine, and a gene resistant to antibiotics such as kanamycin, ampicillin, G418, bleomycin, hygromycin, and chloramphenicol, but not limited thereto.

With regard to the plant expression vector according to one embodiment of the present invention, the promoter can be any of CaMV 35S, actin, ubiquitin, pEMU, MAS, and histone promoter, but not limited thereto. The term "promoter" means a DNA molecule to which RNA polymerase binds in order to initiate its transcription, and it corresponds to a DNA region upstream of a structural gene. The term "plant promoter" indicates a promoter which can initiate transcription in a plant cell. The term "constitutive promoter" indicates a promoter which is active in most of environmental conditions and development states or cell differentiation states. Since a transformant can be selected with various mechanisms at various stages, the constitutive promoter can be preferable for the present invention. Therefore, a possibility for choosing the constitutive promoter is not limited herein.

In the above-described recombinant vector of the present invention, any kind of a typical terminator can be used. Examples include nopalin synthase (NOS), rice α-amylase RAmyl A terminator, phaseoline terminator, and a terminator for octopine gene of *Agrobacterium tumefaciens*, etc., but are not limited thereto.

The present invention also provides a host cell transformed with the aforementioned recombinant vector.

When an eukaryotic cell is transformed with the vector of the present invention, yeast (*Saccharomyces cerevisiae*), an insect cell, a human cell (for example, CHO (Chinese hamster ovary) cell line, W138, BHK, COS-7, 293, HepG2, 3T3, RIN and MDCK cell line), a plant cell, and the like can be used as a host cell. The host cell is preferably a plant cell.

As for the method to deliver the vector of the present invention to a holt cell, the vector can be introduced to a host cell by a microinjection method, calcium phosphate precipitation method, an electroporation method, a liposome-mediated transfection method, DEAE-dextran treatment method, or a gene bombardment method, and the like.

The present invention further provides a method of increasing syringin synthesis in a plant compared to the wild type, comprising transforming a plant cell with the recombinant vector to over-express the UGT72E3/2 gene.

According to the method of one embodiment of the present invention, the UGT72E3/2 gene may consist of the nucleotide sequence of SEQ ID NO: 1, but not limited thereto.

The present invention further provides a transgenic plant with increased syringin production compared to the wild type, in which the plant is transformed with a recombinant vector comprising the gene encoding the recombinant glycosyl transferase UGT72E3/2 protein, which consists of an amino acid sequence of SEQ ID NO: 2.

The present invention further provides a transgenic plant with increased syringin production compared to the wild type, in which the plant is transformed with a recombinant vector comprising the gene encoding the recombinant glycosyl transferase UGT72E3/2 protein which consists of an amino acid sequence of SEQ ID NO: 2 and a recombinant vector comprising the gene encoding the F5H (furulate 5-hydroxylase) protein which consists of an amino acid sequence of SEQ ID NO: 4.

The present invention further provides a transgenic plant with increased syringin production compared to the wild type, in which the plant is transformed with a recombinant vector comprising the gene encoding the recombinant glycosyl transferase UGT72E3/2 protein which consists of an amino acid sequence of SEQ ID NO: 2, a recombinant vector comprising the gene encoding the F5H (furulate 5-hydroxylase) protein which consists of an amino acid sequence of SEQ ID NO: 4, and a recombinant vector comprising the gene encoding the Myb58 protein which consists of an amino acid sequence of SEQ ID NO: 6.

The present invention further provides a transgenic plant with increased syringin production compared to the wild type, in which the plant is transformed with a recombinant vector comprising the gene encoding the recombinant glycosyl transferase UGT72E3/2 protein which consists of an amino acid sequence of SEQ ID NO: 2, a recombinant vector comprising the gene encoding the F5H (furulate 5-hydroxylase) protein which consists of an amino acid sequence of SEQ ID NO: 4, and a recombinant vector comprising the gene encoding the Myb63 protein which consists of an amino acid sequence of SEQ ID NO: 8.

The present invention further provides a transgenic plant with increased syringin production compared to the wild type, in which the plant is transformed with a recombinant vector comprising the gene encoding the recombinant glycosyl transferase UGT72E3/2 protein which consists of an amino acid sequence of SEQ ID NO: 2 and a recombinant vector knock-outing the gene encoding the CHS (chalcone synthase) protein which consists of an amino acid sequence of SEQ ID NO: 10.

In the present invention, for efficient supply of sinapyl alcohol as a substrate for syringin to the transformant over-expressing the recombinant glycosyl transferase UGT72E3/2, each step and working enzymes of the synthesis pathway for syringin were utilized. Specifically, for enhancing the introduction of coumaroyl-CoA to the synthesis pathway for phenylpropanoid, HCT (hydroxycinamoyl-CoA: shikimate/quinqte hydroxycinamoyl transferase) gene was over-expressed and the amount of coniferyl aldehyde converted to coniferyl alcohol is reduced, and for promoting conversion to sinapyl alcohol, the F5H (ferulate 5-hydroxylase) gene was over-expressed. Further, in order to reduce the amount of coumaroyl-CoA lost from the synthesis pathway for syringin to the flavonoid pathway, a mutant deficient of the function of CHS (chalcone synthase) gene was used. For knock-out of the CHS gene, a silencing vector may be used, but it is not limited thereto.

The term "knock-out" as described herein means a modification or a removal of specific gene from a nucleotide sequence to prevent the expression of the specific gene, and it generally indicates a phenomenon in which expression of a gene is down-regulated or completely suppressed.

The present invention further provides a method for producing a transgenic plant with increased syringin synthesis compared to the wild type, comprising:

(a) transforming a plant cell with a recombinant vector comprising the gene encoding the recombinant glycosyl transferase UGT72E3/2 protein which consists of an amino acid sequence of SEQ ID NO: 2, and (b) regenerating a plant from the transgenic plant cell of the step (a).

The present invention further provides a method for producing a transgenic plant with increased syringin production compared to the wild type, comprising (a) producing a transgenic plant over-expressing the UGT72E3/2 protein by transforming a plant with a recombinant vector comprising the gene encoding the recombinant glycosyl transferase UGT72E3/2 protein which consists of an amino acid sequence of SEQ ID NO: 2;

(b) producing a transgenic plant over-expressing the F5H (furulate 5-hydroxylase) protein by transforming a plant with a recombinant vector comprising the gene encoding F5H protein which consists of an amino acid sequence of SEQ ID NO: 4; and (c) cross-breeding the transgenic plant over-expressing the UGT72E3/2 protein of the step (a) and the transgenic plant over-expressing the F5H protein of the step (b) and selecting a transgenic plant which over-expresses simultaneously the UGT72E3/2 protein and F5H protein.

The present invention further provides a method for producing a transgenic plant with increased syringin production compared to the wild type, comprising (a) producing a transgenic plant over-expressing the UGT72E3/2 protein by transforming a plant with a recombinant vector comprising the gene encoding the recombinant glycosyl transferase UGT72E3/2 protein which consists of an amino acid sequence of SEQ ID NO: 2;

(b) producing a transgenic plant over-expressing the F5H (furulate 5-hydroxylase) protein by transforming a plant with a recombinant vector comprising the gene encoding F5H protein which consists of an amino acid sequence of SEQ ID NO: 4;

(c) cross-breeding the transgenic plant over-expressing the UGT72E3/2 protein of the step (a) and the transgenic plant over-expressing the F5H protein of the step (b) and selecting a transgenic plant which over-expresses simultaneously the UGT72E3/2 protein and F5H protein;

(d) producing a transgenic plant over-expressing the Myb58 protein by transforming a plant with a recombinant vector comprising the gene encoding Myb58 protein which consists of an amino acid sequence of SEQ ID NO: 6; and (e) cross-breeding the transgenic plant over-expressing simultaneously the UGT72E3/2 protein and F5H protein of the step (c) and the transgenic plant over-expressing the Myb 58protein of the step (d) and selecting a transgenic plant which over-expresses simultaneously the UGT72E3/2 protein, F5H protein, and Myb58 protein.

The present invention further provides a method for producing a transgenic plant with increased syringin production compared to the wild type, comprising (a) producing a transgenic plant over-expressing the UGT72E3/2 protein by transforming a plant with a recombinant vector comprising the gene encoding the recombinant glycosyl transferase UGT72E3/2 protein which consists of an amino acid sequence of SEQ ID NO: 2;

(b) producing a transgenic plant over-expressing the F5H (furulate 5-hydroxylase) protein by transforming a plant with a recombinant vector comprising the gene encoding F5H protein which consists of an amino acid sequence of SEQ ID NO: 4;

(c) cross-breeding the transgenic plant over-expressing the UGT72E3/2 protein of the step (a) and the transgenic plant over-expressing the F5H protein of the step (b) and selecting a transgenic plant which over-expresses simultaneously the UGT72E3/2 protein and F5H protein;

(d) producing a transgenic plant over-expressing the Myb63 protein by transforming a plant with a recombinant vector comprising the gene encoding Myb63 protein which consists of an amino acid sequence of SEQ ID NO: 8; and (e) cross-breeding the transgenic plant over-expressing simultaneously the UGT72E3/2 protein and F5H protein of the step (c) and the transgenic plant over-expressing the Myb63 protein of the step (d) and selecting a transgenic plant which over-expresses simultaneously the UGT72E3/2 protein, F5H protein, and Myb63 protein.

The present invention further provides a method for producing a transgenic plant with increased syringin production compared to the wild type, comprising (a) producing a transgenic plant over-expressing the UGT72E3/2 protein by transforming a plant with a recombinant vector comprising the gene encoding the recombinant glycosyl transferase UGT72E3/2 protein which consists of an amino acid sequence of SEQ ID NO: 2;

(b) producing a plant in which the gene encoding the CHS (chalcone synthase) protein consisting of an amino acid sequence of SEQ ID NO: 10 is knocked out; and (c) cross-breeding the transgenic plant over-expressing the UGT72E3/2 protein of the step (a) and the plant with knocked-out CHS protein-coding gene of the step (b) and selecting a transgenic plant which over-expresses the UGT72E3/2 protein and suppresses expression of the CHS protein.

With the method according to one embodiment of the present invention, the plant exhibits increased syringin synthesis preferably in the leaves or roots, or most preferably in the leaves, but it is not limited thereto.

The method of the present invention comprises a step of transforming a plant cell with the recombinant vector of the present invention, and the transformation may be mediated by *Agrobacterium tumefaciens*. Further, the method of the present invention comprises a step of regenerating a transgenic plant from the transgenic plant cell. As for the method for regenerating a transgenic plant from a transgenic plant cell, a method well known in the pertinent art can be used.

The transgenic plant cell needs to be regenerated into a whole plant. Techniques for regeneration into a mature plant by culture of callus or protoplast are well known in the pertinent art for various species (Handbook of Plant Cell Culture, Vol. 1-5, 1983-1989 Momillan, N.Y.).

The Myb58 gene used in the present invention is a transcription factor for positive regulation of the genes that are involved with the biosynthesis pathway of phenylpropanoid, and Myb63 known to have a similar function is also expected to exhibit the synergistic effect in the process of syringin synthesis.

The present invention further provides a transgenic plant with increased syringin production compared to the wild type, which is produced by each method described above, and a seed thereof.

With regard to the plant according to one embodiment of the present invention, the plant can be preferably a dicot plant such as *Arabidopsis thaliana*, tobacco, eggplant, pepper, tomato, burdock, crown daisy, lettuce, balloon flower, spinach, chard, yam, celery, carrot, water parsley, parsley, Chinese cabbage, cabbage, *Raphanus sativus* for. raphnistroides MAK, watermelon, oriental melon, cucumber, zucchini, gourd, strawberry, soybean, mung bean, kidney bean, or sweet pea. Most preferably, it can be *Arabidopsis thaliana*, but it is not limited thereto.

The present invention still further provides a composition for increasing syringin synthesis in a plant comprising, as an effective component, a recombinant vector comprising the gene consisting of SEQ ID NO: 1 which encodes the UGT72E3/2 protein. The composition comprises, as an effective component, the recombinant vector comprising the gene consisting of SEQ ID NO: 1 which encodes the UGT72E3/2 protein, and according to transformation of a plant with the recombinant vector, it is possible to increase the syringin synthesis in plant.

Herein below, the present invention is explained in greater detail in view of the Examples. However, it is evident that the following Examples are given only for exemplification of the present invention and by no means the present invention is limited to the following Examples.

Information of Genes and Nucleotide Sequences used in the Present Invention

Information of the genes and nucleotide sequences that are used in the present invention is as described in the following Table 1.

TABLE 1

| Gene name | Nucleotide sequence number | Amino acid sequence number |
|---|---|---|
| UGT72E3/2 | 1 | 2 |
| F5H | 3 | 4 |
| Myb58 | 5 | 6 |
| Myb63 | 7 | 8 |
| CHS | 9 | 10 |
| HCT | 11 | 12 |

EXAMPLE 1

Primary and Secondary Structures of *Arabidopsis Thaliana* Glycosyl Transferase UGT72E2 and UGT72E3

In order to develop a new glycosyl transferase which is useful for in-plant production of syringin having various pharmaceutical applications, a comparison of primary and secondary structures is made between UGT72E2 having very excellent glycosyl transferase efficiency but poor substrate specificity for coniferyl alcohol, which is a precursor of syringin, and UGT72E3 protein having very excellent substrate specificity for sinapyl alcohol but poor glycosyl transferase efficiency, by using SWISS-MODEL workspace (FIG. 1). As a pre-step for the domain swapping to produce a new recombinant glycosyl transferase having all the advantages of both enzymes, a difference in the primary and secondary structures of the carboxy terminal containing PSPG motif that is important for glycosyl transferase activity and the amino terminal for determining the substrate specificity and the region in which domain swapping occurs were marked.

EXAMPLE 2

Tertiary Structure of *Arabidopsis Thaliana* Glycosyl Transferase UGT72E2 and UGT72E3, and Newly Produced Recombinant Glycosyl Transferase UGT72E2/3 and UGT72E3/2

Figure 2:
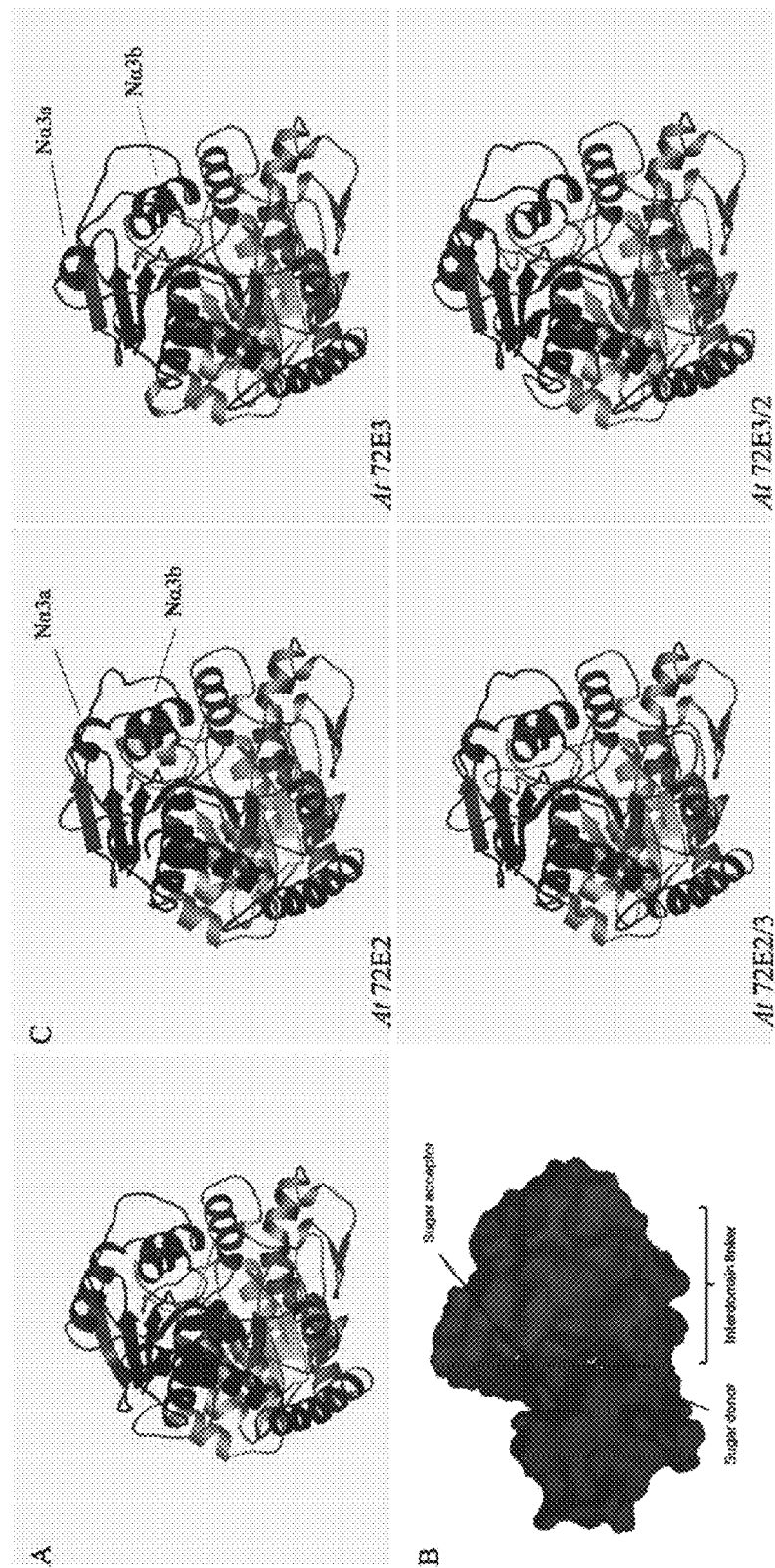
FIG. 2 is a drawing illustrating the comparison of the tertiary structure of glycosyl transferase UGT72B1(A) and VvGT1(B) that are derived from *Arabidopsis thaliana* or grape, glycosyl transferase UGT72E2 and UGT72E3 that are derived from *Arabidopsis thaliana*, and the recombinant glycosyl transferase UGT72E2/3 and UGT72E3/2(C) which have been produced in the present invention.

As it is shown from glycosyl transferase UGT72B1 and VvGT1 derived from *Arabidopsis thaliana* and grape, respectively, of which tertiary structure has been already studied thoroughly, a glycosyl transferase generally has a region for determining substrate specificity (i.e., sugar acceptor) and a region for determining glycosyl transferase activity (i.e., sugar donor), which are adjacent to each other in a deep and narrow gap at a boundary between the amino terminal domain and carboxy terminal domain (FIGS. 2A and 2B). By using SWISS-MODEL workspace, the expected tertiary structure of UGT72E2, UGT72E3, UGT72E2/3 and UGT72E3/2 was obtained (FIG. 2C). It is believed that a structural change near the region for determining the substrate specificity and the region for determining the glycosyl transferase activity is involved with a difference in the substrate specificity and glycosyl transferase activity among glycosyl transferases of UGT72E2, UGT72E3, UGT72E2/3 and UGT72E3/2.

EXAMPLE 3

Recombinant Vector used for Transformant Production, Expression Level of Gene Transferred to Transformant, and Phenotype of Transformant in Response to UV Rays Inventors of the present invention investigated, among one hundred glycosyl transferases of *Arabidopsis thaliana*, the enzyme characteristics of the glycosyl transferase UGT72E clade which has been reported to have an ability of transferring a sugar to sinapyl alcohol as a precursor of syringin or structurally similar coniferyl alcohol. UGT72E clade also has structural characteristics that are similar to those of a common glycosyl transferase. The amino terminal domain has a region for substrate recognition and the carboxy terminal has an enzyme activated region for transferring a sugar activated by UDP to a substrate. In particular, PSPG (Plant Secondary Product Glucosyl transferase) motif at the carboxy terminal is reported to be important for the activity of a glycosyl transferase derived from a plant. The UGT72E clade includes glycosyl transferase UGT72E1, UGT72E2 and UGT72E3 having similar nucleotide sequence.

In the present invention, each of the UGT72E2 and UGT72E3 was divided into an amino fragment including the amino acids from number 1 to number 344 and a carboxy fragment including the amino acids from number 345 to number 481. The amino fragment includes a region for determining the substrate recognition specificity and the carboxy terminal includes the PSPG motif, which is important for glycosyl transferase activity. For efficient production of syringin in a plant, the substrate specificity is more important than the glycosyl transferase activity. Thus, instead of having a precise half-cut, a large amino fragment is prepared to include ¾ of the entire length while the carboxy fragment is prepared to as a small fragment including PSPG motif.

The recombinant UGT72E2/3 gene used in the present invention was prepared by linking an amino fragment including the amino acids from number 1 at the amino terminal to number 344 of UGT72E2 to a carboxy fragment including the amino acids from number 345 to number 481 at the carboxy terminal of UGT72E3. The recombinant UGT72E3/2 gene was prepared by linking an amino fragment including the amino acids from number 1 at the amino terminal to number 344 of UGT72E3 to a carboxy fragment including the amino acids from number 345 to number 481 at the carboxy terminal of UGT72E2.

In the present invention, a binary vector was constructed such that the coding regions of UGT72E2 and UGT72E3 genes isolated from *Arabidopsis thaliana* and the recombinant UGT72E2/3 and UGT72E3/2 genes, which have been newly produced in the present invention, are controlled by CaMV35S promoter and a super promoter. The resulting vector was incorporated into *A. tumefaciens* EHA105, and then *Arabidopsis thaliana* was transformed with the bacteria using an in planta method (FIG. 3).

Because the phenotype of a transformant is significantly affected by expression level of an introduced transfer gene, among the *Arabidopsis thaliana* transformants with hygromycin resistance, the expression amount resulting from stable introduction of the transferase genes UGT72E2, UGT72E3, UGT72E2/3 and UGT72E3/2 derived from *Arabidopsis thaliana* was determined based on RT-PCR. For specific amplification of the introduced gene, a combination of UGT72E gene-specific forward primer (5'GGTTG-GAGCTCGACGTTGGAAAGCGTC 3'; SEQ ID NO: 13) and a reverse primer (5'TTAAAGCAGGGCATGCCTGC 3'; SEQ ID NO: 14) specific to 3' UTR region of the vector was used. For correction of relative RNA amount, Actin 1 gene from *Arabidopsis thaliana*, which is always expressed at constant level, was used as a reference gene. Among fifteen transformants for each gene which has been determined, transformant lines having similar expression of UGT72E2, UGT72E3, UGT72E2/3 and UGT72E3/2 were finally identified (FIG. 3B).

Conversion of sinapyl alcohol to syringin according to activation of a glycosyl transferase in leaves reduce the production of sinapyl ester which absorbs UV rays in leaves. As such, when the leaves of a transformant with enhanced glycosyl transferase activity is exposed to UV rays, UV rays are mostly absorbed by chlorophylls to exhibit a very strong red color. When production of sinapyl ester occurs normally in leaves, the UV ray absorption amount by chlorophylls is reduced to exhibit a very weak red color (FIG. 3C).

EXAMPLE 4

Figure 4:
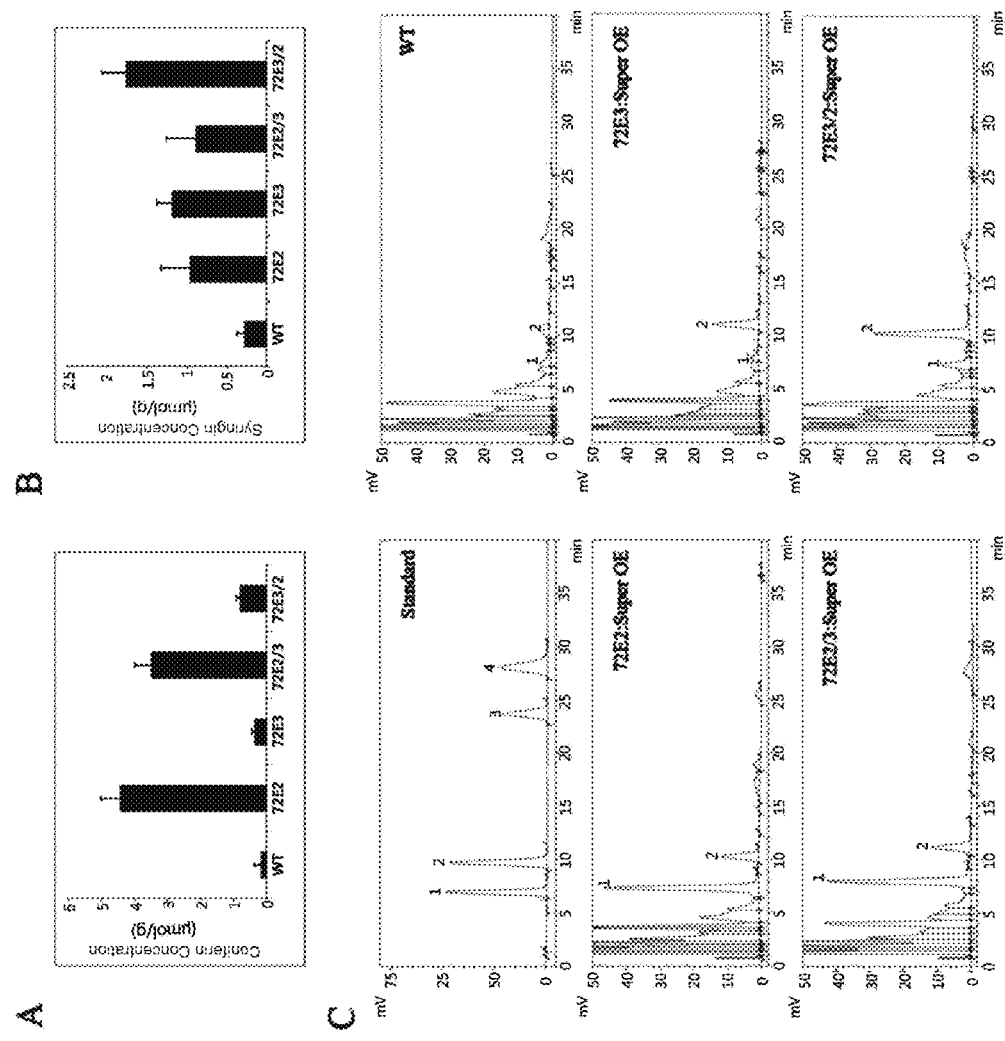
FIG. 4 is a drawing illustrating the quantitative HPLC analysis of the production of coniferin and syringin in leaves of the wild type *Arabidopsis thaliana* and the transformants, which express each of the four glycosyl transferase genes, i.e., UGT72E2, UGT72E3, UGT72E2/3, and UGT72E3/2 (peak of each chromatogram in (C): 1, coniferyl alcohol 4-O-glucoside (coniferin); 2, sinapyl alcohol 4-O-glucoside (syringin); 3, coniferyl alcohol; and 4, sinapyl alcohol).

Quantitative HPLC Analysis of Coniferin and Syringin Production in Leaves of Transformant Monolignol produced by activation of synthesis pathway for phenylpropanoid in leaves of an angiosperm plant is mostly present as coniferyl alcohol, which is converted to coniferin by a glycosyl transferase. With an enzyme action, an extremely small portion of coniferyl alcohol is converted to sinapyl alcohol as a precursor of syringin, and rate of conversion to syringin caused by glycosyl transferase is very low due to low enzyme activity. Most of the sinapyl alcohol is converted to sinapyl ester which has an activity of protecting leaves by absorbing UV rays. As such, the over-expression of UGT72E2 gene having high substrate specificity for coniferyl alcohol increases coniferin production and over-expression of UGT72E3 having high substrate specificity for sinapyl alcohol relatively increases production of syringin (FIGS. 4A and 4B). Over-expression of the recombinant gene UGT72E3/2 exhibited the effect of increasing syringin production in plant by 48.7% compared to the over-expression of the UGT72E3 gene (FIGS. 4B and 4C).

EXAMPLE 5

Figure 5:
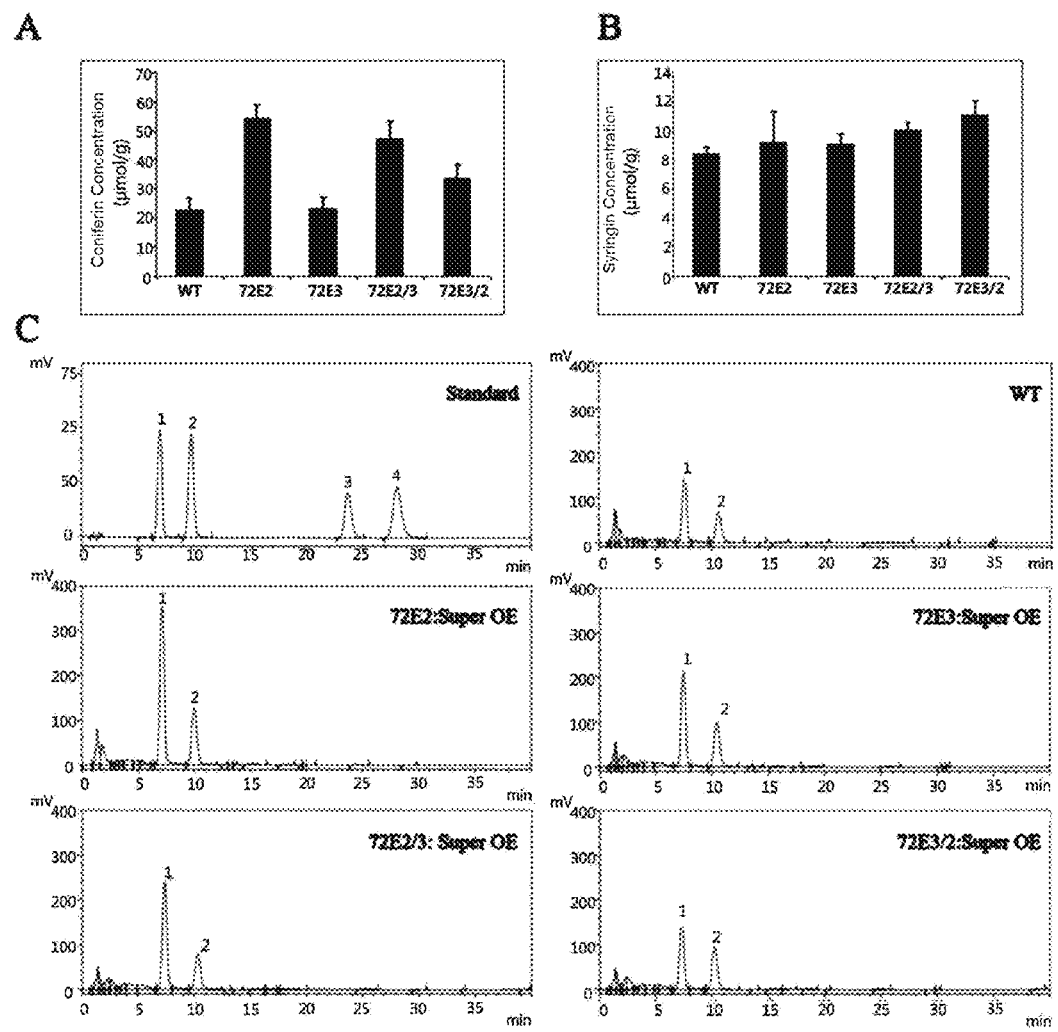
FIG. 5 is a drawing illustrating the quantitative HPLC analysis of the production of coniferin and syringin in roots of the wild type *Arabidopsis thaliana* and the transformants, which express each of the four glycosyl transferase genes, i.e., UGT72E2, UGT72E3, UGT72E2/3, and UGT72E3/2 (peak of each chromatogram in (C): 1, coniferyl alcohol 4-O-glucoside (1, coniferyl alcohol 4-O-glucoside (coniferin); 2, sinapyl alcohol 4-O-glucoside (syringin); 3, coniferyl alcohol; and 4, sinapyl alcohol).

Quantitative HPLC Analysis of Coniferin and Syringin Production in Roots of Transformant Unlike the leaves that are constantly exposed to light, once exposed to light, the roots of a plant show increased expression of various genes that are involved with the synthesis pathway for phenylpropanoid based on a signal transduction mechanism. As a result, synthesis of monolignols including a great amount of coniferyl alcohol and sinapyl alcohol is enhanced. Although the production of coniferin and syringin that have been hardly detected in leaves of the wild type plant cultivated under same condition was significantly increased, the production rate of syringin was still low, i.e., only 25% of the coniferin. Further, although the production of coniferin was increased by two or more times in the roots of a transformant which over-expresses UGT72E2 having high glycosyl transferase activity and strong substrate specificity for coniferyl alcohol, there was no big change in syringin production (FIGS. 5B and 5C). In the roots of a transformant which over-expresses UGT72E3 gene having weak glycosyl transferase activity but strong substrate specificity for sinapyl alcohol, coniferin and syringin were produced at almost the same level as those of the wild type. However, the over-expression of the recombinant gene UGT72E3/2 exhibited the effect of increasing syringin production in the roots by 11.7% compared to the over-expression of the UGT72E3 gene (FIGS. 5B and 5C).

EXAMPLE 6

Nucleotide Sequence and Amino Acid Sequence of Glycosyl Transferase UGT72E3/2

Nucleotide sequence of the new recombinant glycosyl transferase UGT72E3/2 gene and the amino acid sequence of the protein encoded by the nucleotide sequence, which exhibits the glycosyl transferase activity enhanced by 48.7% or more compared to the conventionally known glycosyl transferase UGT72E3 while maintaining the substrate specificity for sinapyl alcohol, are shown in FIG. 6.

EXAMPLE 7

Comparison of Activity of Glycosyl Transferases that are Present in Protein Extract Prepared from Leaves of Wild Type and Transgenic *Arabidopsis Thaliana* Over-Expressing Each of the Glycosyl Transferase UGT72E2, UGT72E3, UGT72E2/3, and UGT72E3/2

Most of monolignols produced by activation of synthesis pathway for phenylpropanoid in leaves of an angiosperm plant are present as coniferyl alcohol, and it is converted to coniferin while only an extremely small portion is converted to sinapyl alcohol as a precursor of syringin by continuous enzyme action by F5H (furulate 5-hydroxylase), COMT (caffeic acid 3-O-methyltransferase) and CAD. As such, supply of sinapyl alcohol as a substrate is an important factor for determining syringin production together with the activity of glycosyl transferase.

Figure 7:
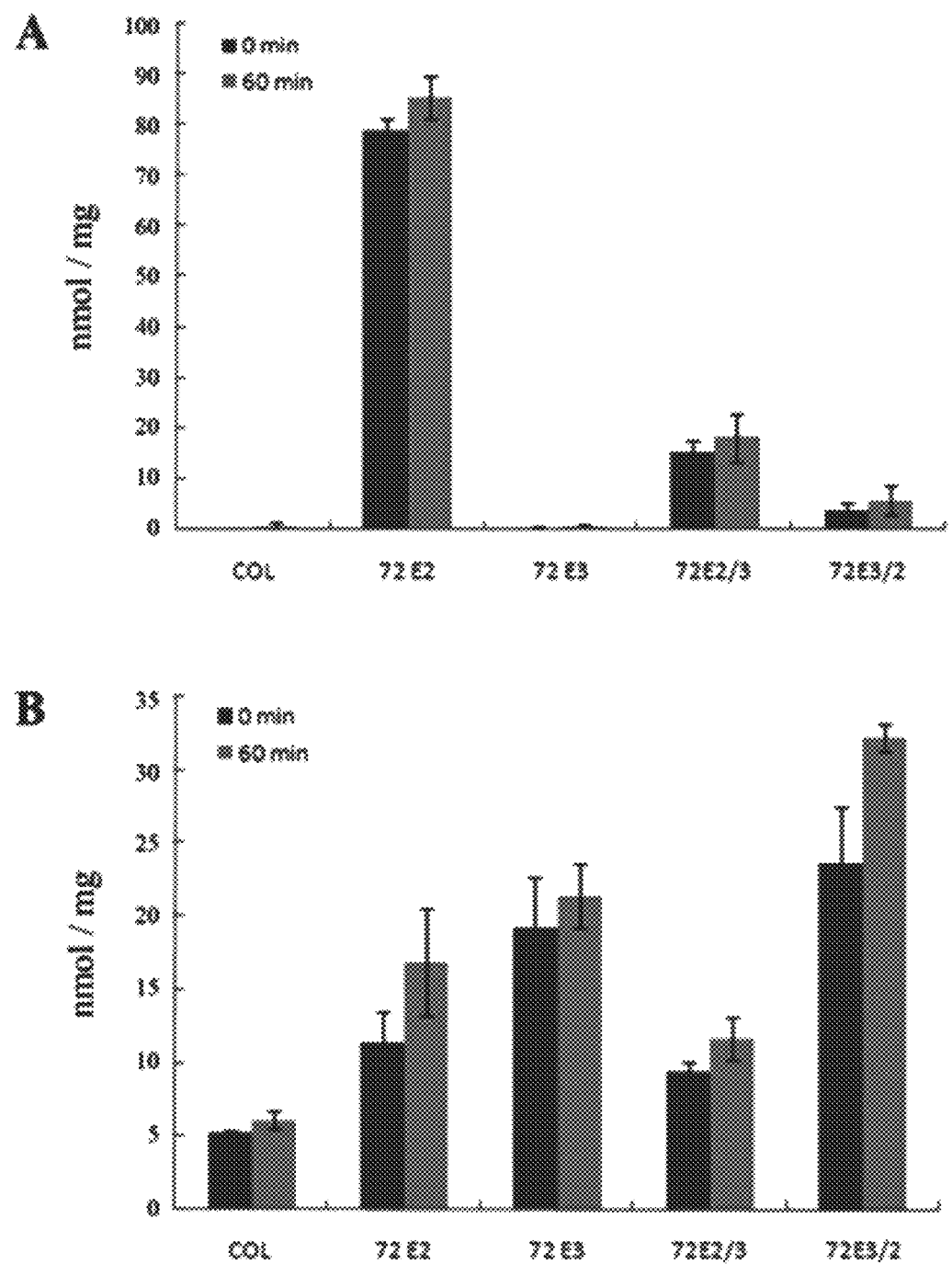
FIG. 7 is a drawing illustrating the results of comparing the activity of glycosyl transferase, which is present in a protein extract prepared from the leaves of the *Arabidopsis thaliana* transformant over-expressing each of the glycosyl transferase UGT72E2, UGT72E3, UGT72E2/3 and UGT72E3/2, or the wild type, in which the activity of the glycosyl transferase present in the protein extract of each transformant was indirectly measured by determining coniferin and syringin, that are produced 60 minutes after adding coniferyl alcohol or sinapyl alcohol to the protein extract of the leaves of the transgenic plant. (A) Production amount of coniferin and (B) production amount of syringin.

In order to compare the activity of the glycosyl transferases, 1 mM coniferyl alcohol or sinapyl alcohol and 5 mM UDP-glucose were added as a substrate to a protein extract prepared from leaves of wild type and transgenic *Arabidopsis thaliana* over-expressing each of the glycosyl transferase UGT72E2, UGT72E3, UGT72E2/3, and UGT72E3/2. Then, the reaction was allowed to occur at 22° C. for 60 minutes. After that, methanol (2× volume) was added to the reaction solution to terminate the reaction, and by using HPLC, coniferin and syringin produced before and after the reaction were quantified by HPLC. As it has been previously shown under in vivo conditions, the recombinant glycosyl transferase UGT72E3/2 has high substrate specificity for sinapyl alcohol and high glycosyl transferase activity. In particular, UGT72E3/2 exhibited better syringin production speed according to addition of substrate than other glycosyl transferases (FIG. 7).

The above results demonstrate that, by also using a method of increasing supply of sinapyl alcohol based on a metabolic engineering means to a transformant over-expressing UGT72E3/2, syringin can be produced in a plant at high efficiency.

EXAMPLE 8

Figure 8:
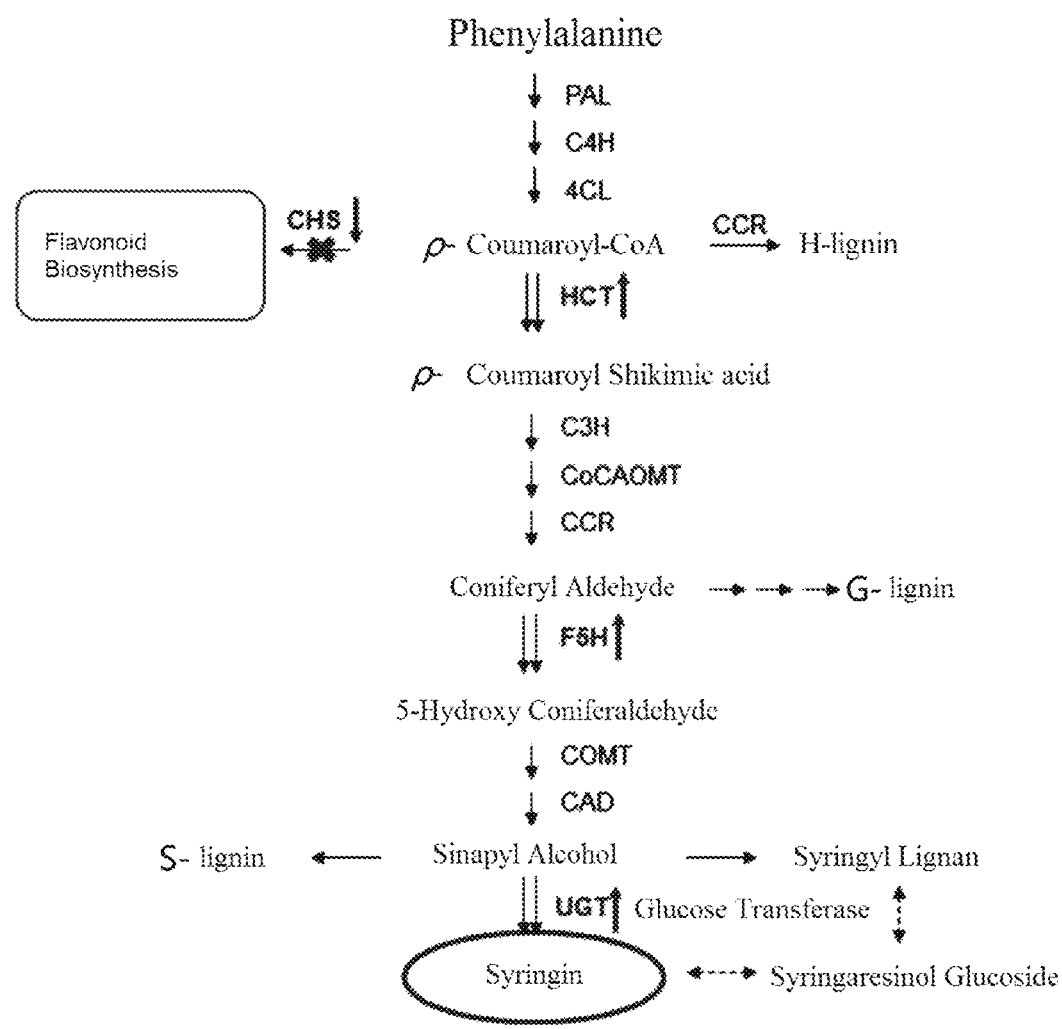
FIG. 8 is a drawing illustrating the phenylpropanoid synthesis pathway for synthesis of syringin and the regulation site of the gene that is used in the present invention.

Synthesis Pathway for Phenylpropanoid and Gene Regulation Site for Syringin Synthesis For efficient supply of sinapyl alcohol as a substrate for syringin to a transformant over-expressing the recombinant glycosyl transferase UGT72E3/2 with use of a metabolic engineering means, each step and working enzymes of the synthesis pathway for phenylpropanoid were utilized. Specifically, in order to reduce the amount of coumaroyl-CoA lost from the synthesis pathway for syringin to the flavonoid pathway, a mutant deficient of CHS (chalcone synthase) gene was used. Further, for enhancing the introduction of coumaroyl-CoA to the synthesis pathway for phenylpropanoid, HCT (hydroxycinamoyl-CoA: shikimate/quinqte hydroxycinamoyl transferase) gene was over-expressed, and the amount of coniferyl aldehyde converted to coniferyl alcohol is reduced, and for promoting conversion to sinapyl alcohol, a strategy of over-expressing the F5H (ferulate 5-hydroxylase) gene was employed (FIG. 8).

EXAMPLE 9

Production of Transgenic *Arabidopsis Thaliana* Over-Expressing HCT, F5H and Myb58 as a Gene for Regulating Synthesis Pathway for Phenylpropanoid and Determination of Expression Amount of Each Gene A binary vector was constructed such that the coding regions of HCT, F5H and Myb58 of *Arabidopsis thaliana* are regulated by a super promoter. After introducing the vector to *Agrobacterium tumefaciens* EHA105, transformation of *Arabidopsis thaliana* was performed by in planta method using the aforementioned bacteria. At that time, for the purpose of having pyramidal accumulation of HCT, F5H and Myb58 genes in the UGT72E3/2 over-expressing transformant, which has been produced by using hygromycin resistant selection marker, by a cross-breeding and selection mode, the *Arabidopsis thaliana* transformant of each gene was prepared by using kanamycin (HCT and F5H) or herbicide (Myb58) resistant selection marker.

Because the phenotype of a transformant is significantly affected by expression level of an introduced transfer gene, among the transformants which have been selected, the expression amount resulting from stable introduction of HCT, F5H and Myb58 genes was determined based on RT-PCR. For specific amplification of the introduced gene, a combination of HCT gene-specific forward primer HCT-F (5'-CTGGTTACTTTGGGAATGTGATATTCAC-3'; SEQ ID NO: 15), F5H gene-specific forward primer a F5H-F (5'-CAGACGAGTTGAAGAATCCGACATCGAG-3'; SEQ ID NO: 16), and Myb58 gene-specific forward primer Myb58-F (5'-CAGACGAGTTGAAGAATCCGACATC-GAG-3; SEQ ID NO: 17) were used. Further, as a reverse primer, UTR-R (5'TTAAAGCAGGGCATGCCTGC 3'; SEQ ID NO: 14) specific to 3' UTR region of the vector was used. For calibration of the relative amount of RNA, Actin 2 gene of *Arabidopsis thaliana*, which is always expressed at constant level, was used as a reference gene. Ten transformants were examined for each gene, and as a result, transformant lines having excellent expression of HCT, F5H and Myb58 were finally obtained (FIG. 9). Meanwhile, there is only one CHS gene present *Arabidopsis thaliana*, and when this gene is deficient, color of the seed coat turns into yellow color. Based on such difference in the phenotype, the homozygous transformant was isolated.

EXAMPLE 10

Quantitative HPLC Analysis of Coniferin and Syringin Production in Leaves and Roots of Transformant Via the synthesis pathway for phenylpropanoid, an angiosperm plant produces the following three kinds of monolignol; i.e., H monolignol using p-coumaryl alcohol, G monolignol using coniferyl alcohol, and S monolignol using sinapyl alcohol. However, most monolignols are present in G monolignol form, and thus the concentration of coniferyl alcohol is relatively the highest in a plant cell. Over expression of the glycosyl transferase UGT72E2 yields conversion of coniferyl alcohol at high concentration to coniferin. Because part of coniferyl alcohol is converted to sinapyl alcohol due to the enzyme action of F5H and COMT (caffeic acid 3-O-methyltransferase), concentration of sinapyl alcohol as a precursor of syringin is very low in a plant cell. Thus, for efficient production of syringin in a plant cell, a metabolic engineering approach for increasing sinapyl alcohol in addition to having glycosyl transferase UGT72E3/2 with high efficiency is needed.

In order to examine a synergistic effect between the glycosyl transferase UGT72E3/2 gene and the HCT, F5H and CHS genes, quantitative HPLC analysis of coniferin and syringin production in leaves and roots of the transformant was performed. Specifically, a transformant over-expressing HCT or F5H, which regulates an important step of the synthesis pathway for phenylpropanoid, was produced and subjected to cross-breeding with the transformant over-expressing the glycosyl transferase UGT72E3/2 with high efficiency. After that, a transformant over-expressing HCT and UGT72E3/2 or F5H and UGT72E3/2 was separated at F2 generation, and the homozygous line was obtained from the next generation. Further, for preventing the loss of p-coumaroyl-CoA as an important precursor of the synthesis pathway for phenylpropanoid to the synthesis pathway for flavonoid, a mutant deficient of CHS (chalcone synthase), which is responsible for conversion of p-coumaroyl-CoA to chalcone, and the transformant over-expressing UGT72E3/2 were subjected to cross-breeding. After isolating the line with knocked-out CHS gene and over-expressed UGT72E3/2 gene from F2 generation, the homozygous line was confirmed from the next generation.

Figure 10:
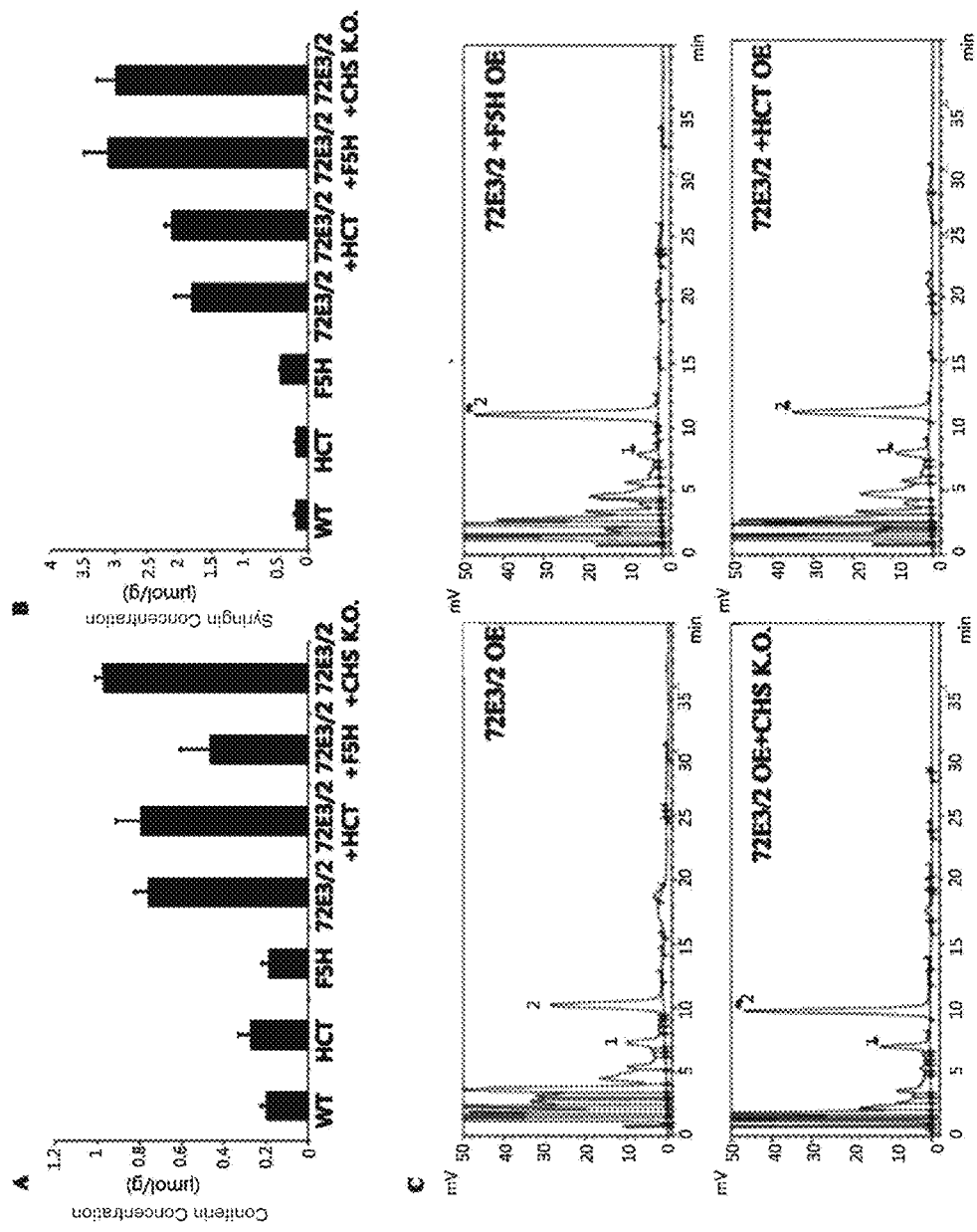
FIG. 10 is a drawing illustrating the quantitative HPLC analysis of the production of (A) coniferin and (B) syringin in leaves of the transformants including wild type, which express various combinations of the genes, for determining the synergistic effect between the glycosyl transferase UGT72E3/2 and the HCT, F5H and CHS genes of the synthesis pathway for phenylpropanoid. Peak 1 of each chromatogram in (C) indicates coniferyl alcohol 4-O-glucoside (coniferin) and peak 2 indicates sinapyl alcohol 4-O-glucoside (syringin).

As a result of determining the efficiency of syringin synthesis in leave and roots of the transformant by using HPLC, it was found that, compared to the transformant in which only the UGT72E3/2 gene is over-expressed, the syringin synthesis was increased by 17.3%, 71.3% and 64.6%, respectively, in the leaves of the plant with over-expressed HCT or over-expressed F5H, but with deficient CHS gene function (FIG. 10).

Figure 11:
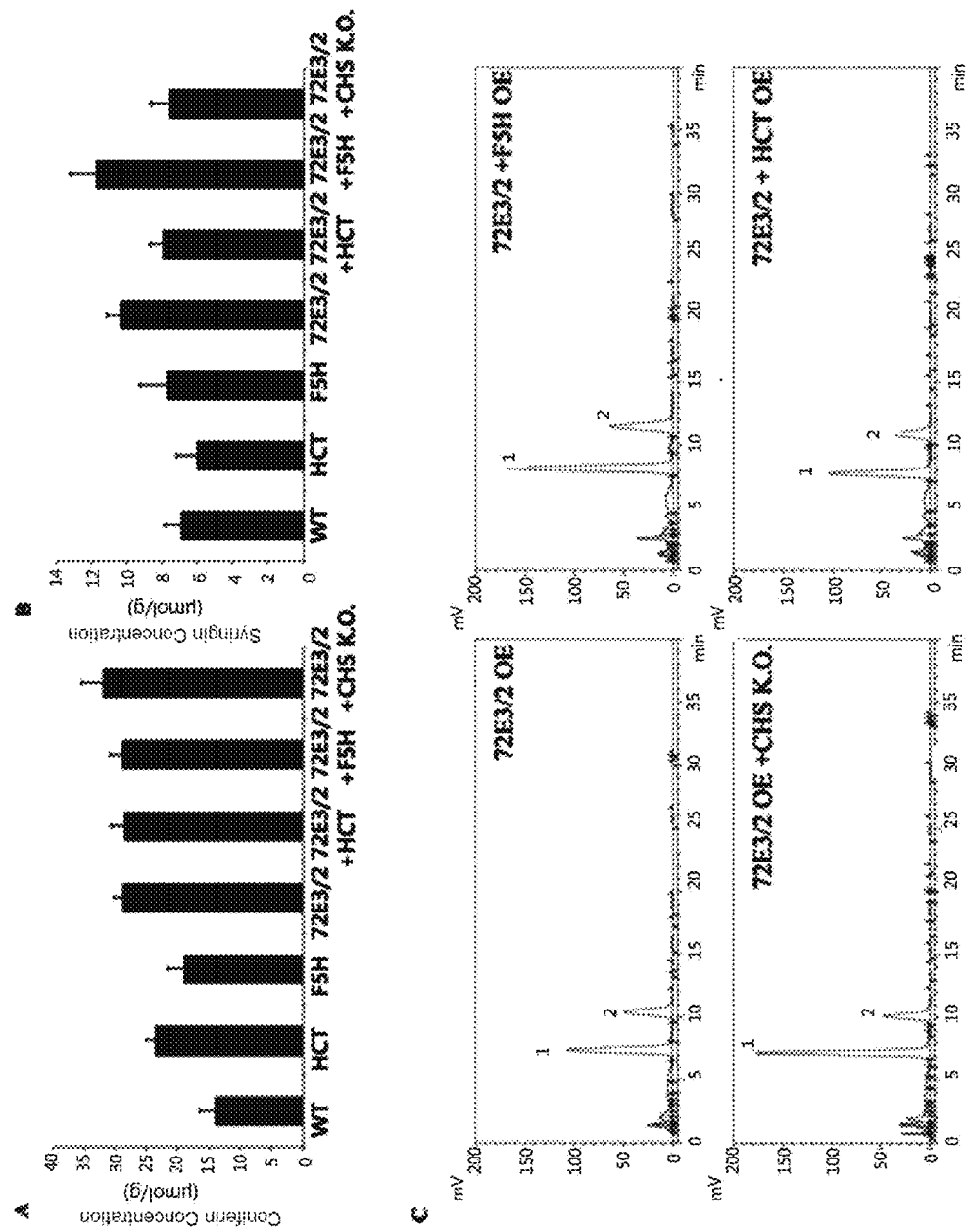
FIG. 11 is a drawing illustrating the quantitative HPLC analysis of the production of (A) coniferin and (B) syringin in roots of the transformants including wild type, which express various combinations of the genes, for determining the synergistic effect between the glycosyl transferase UGT72E3/2 and the HCT, F5H and CHS genes of the synthesis pathway for phenylpropanoid. Peak 1 of each chromatogram in (C) indicates coniferyl alcohol 4-O-glucoside (coniferin) and peak 2 indicates sinapyl alcohol 4-O-glucoside (syringin).

However, from the roots of the plant, only the transformant line having over-expression of UGT72E3/2 and F5H showed slightly increased syringin synthesis compared to the transformant in which only the UGT72E3/2 gene is over-expressed (FIG. 11).

EXAMPLE 11

Quantitative HPLC Analysis of Syringin Production in Leaves and Roots of Transformant Based on Synergistic Effect using Pyramiding of UGT72E3/2, F5H and Myb58 Genes Accumulated over-expression of the new glycosyl transferase gene UGT72E3/2 having high specificity for sinapyl alcohol, which has been developed by an enzyme engineering method, and F5H gene involved with conversion of coniferyl alcohol to sinapyl alcohol in the phenylpropanoid pathway exhibited the effect of remarkably increasing the syringin production rate. Meanwhile, when exposed to light, roots of a plant exhibit increased expression of various genes that are involved with the synthesis pathway of phenylpropanoid based on a light signal transduction mechanism. As a result, synthesis of monolignols including a large amount of coniferyl alcohol and sinapyl alcohol is enhanced, and thus the synthesis amount of syringin in roots of the wild type plant is at least 36 times higher than that of the leaves. Meanwhile, the production amount of syringin in leaves of the transformant which over-expresses UGT72E3/2 and F5H is increased by 16 times or more than that of the leaves of the wild type. However, compared to the syringin amount produced in the roots of the transformant, it is still lower by a factor of at least 4. Increasing the syringin production in leaves has an advantage that, unlike roots, a large scale production can be made without destroying a plant. As such, like the roots exposed to light, a method of increasing various genes involved with the phenylpropanoid synthesis is also needed for leaves.

In order to solve the aforementioned problems, syringin production by a transformant based on synergistic effect using pyramiding of the glycosyl transferase UGT72E3/2 gene, F5H gene of the synthesis pathway for phenylpropanoid, and Myb58 gene as a transcription factor for positive regulation of the genes relating to the synthesis pathway of lignin was measured in the present invention by quantitative HPLC analysis.

Figure 12:
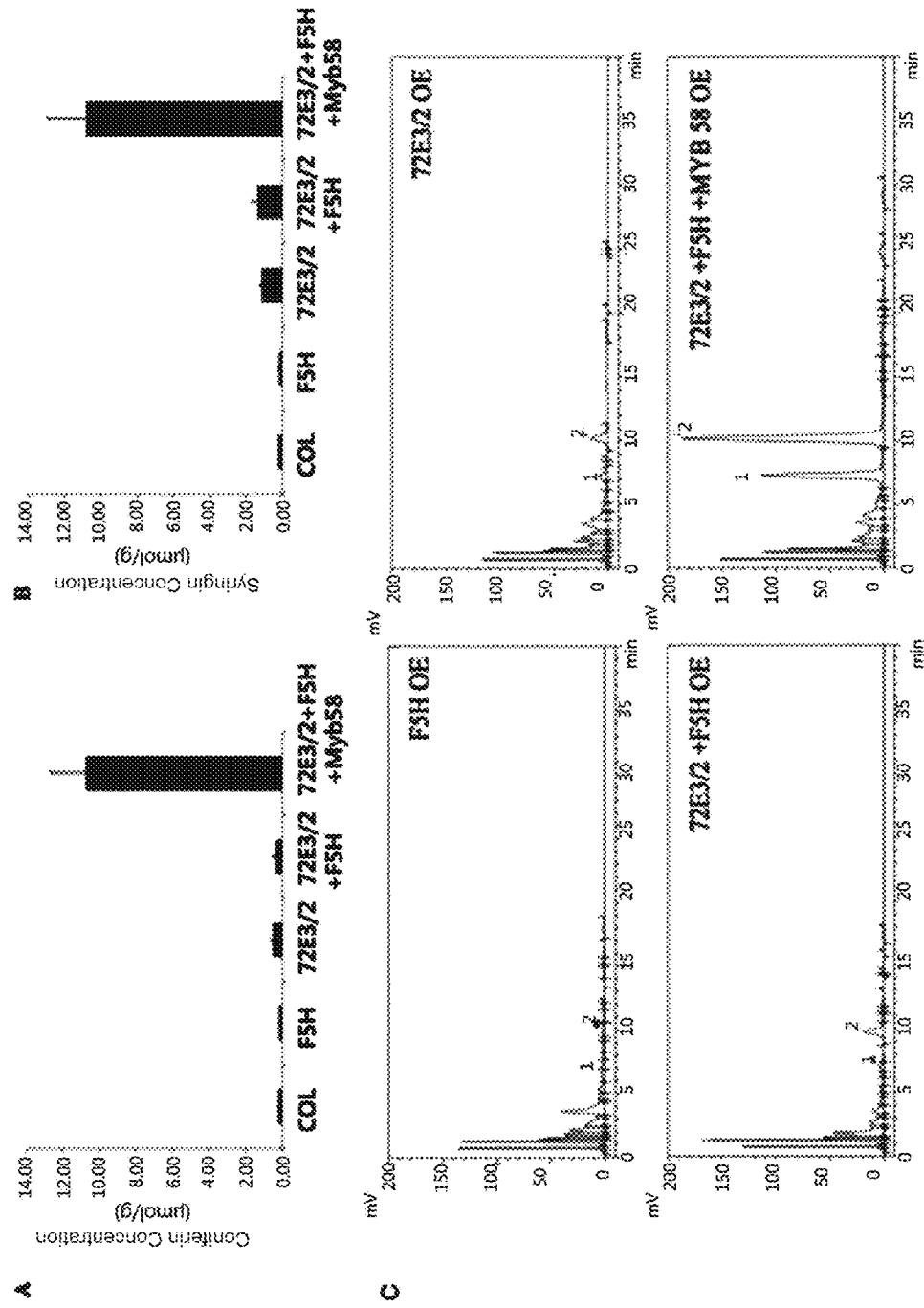
FIG. 12 is a drawing illustrating the quantitative HPLC analysis which shows a dramatic increase in the production of (A) coniferin and (B) syringin in the transformant leaves as caused by the synergistic effect based on pyramiding of the glycosyl transferase UGT72E3/2, the F5H gene in the synthesis pathway for phenylpropanoid, and the Myb58 gene as a transcription factor for positive regulation of the genes involved with the synthesis pathway for lignin. Peak 1 of each chromatogram in (C) indicates coniferyl alcohol 4-O-glucoside (coniferin) and peak 2 indicates sinapyl alcohol 4-O-glucoside (syringin).
Figure 13:
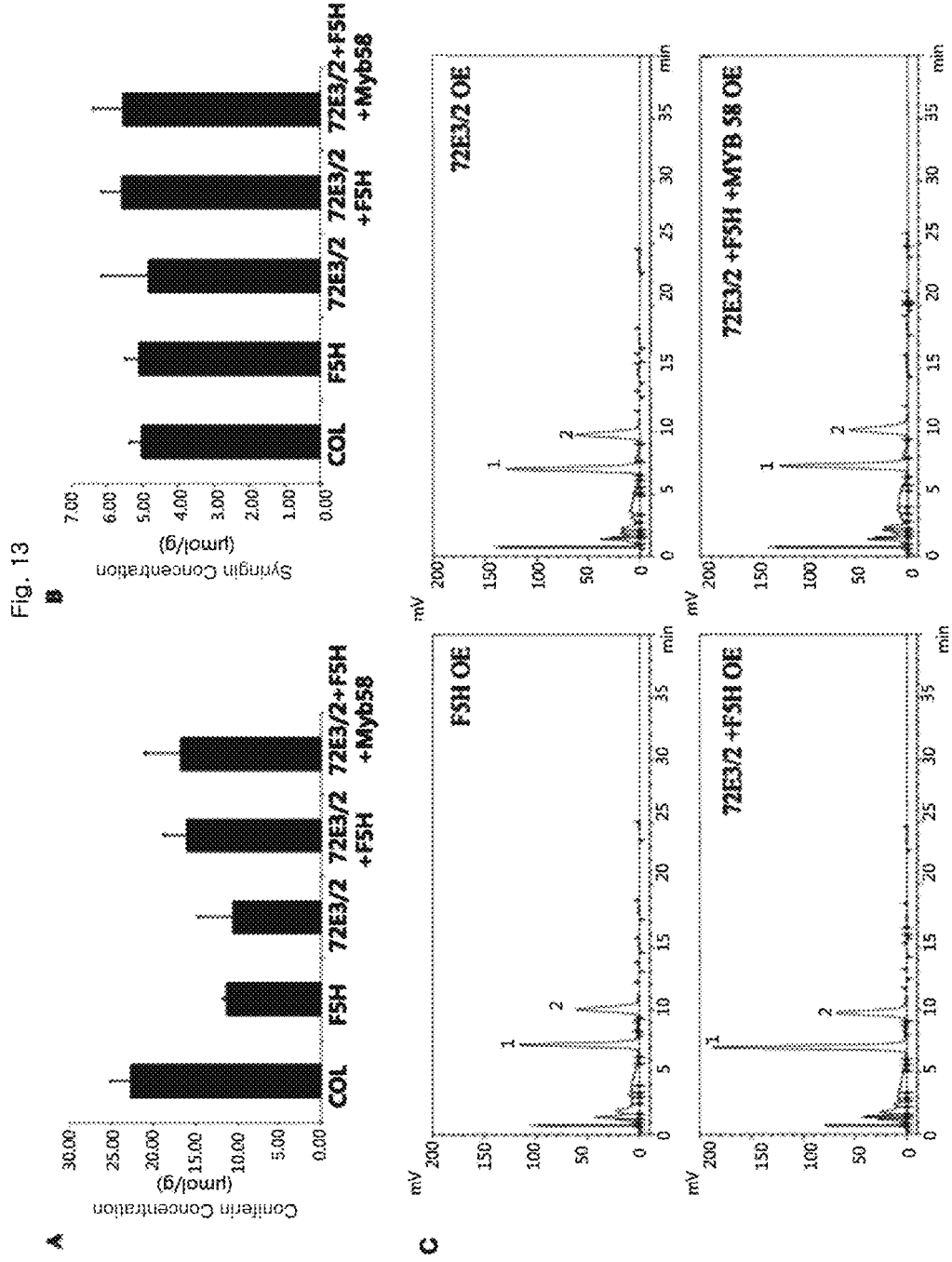
FIG. 13 is a drawing illustrating the result of HPLC analysis which shows that the synergistic effect based on accumulation of the glycosyl transferase UGT72E3/2, the F5H gene in the synthesis pathway for phenylpropanoid, and the Myb58 gene as a transcription factor for positive regulation of the genes involved with the synthesis pathway for lignin has no significant effect in the roots of the transformant. Peak 1 of each chromatogram in (C) indicates coniferyl alcohol 4-O-glucoside (coniferin) and peak 2 indicates sinapyl alcohol 4-O-glucoside (syringin).

To confirm the synergistic effect using the Myb58 gene, a transformant over-expressing the Myb58 gene as a specific transcription factor for positive regulation of the synthesis pathway of lignin in Arabidopsis thaliana was produced. Since the Myb58 gene cannot enhance the expression of F5H gene, after cross-breeding with a transformant which over-expresses both UGT72E3/2 and F5H genes, a transformant line which over-expresses all of the Myb58, UGT72E3/2 and F5H genes was selected at F2 generation and the homozygous line was obtained at the next generation. As a result of investigating the efficiency for syringin synthesis in the leaves and roots of those transformants by using HPLC, it was found that, in the leaves of the transformant in which all of the UGT72E3/2, F5H, and Myb58 genes are over expressed, the production amount of syringin is increased by 8 times compared to the transformant in which UGT72E3/2 and F5H genes are over-expressed, or by 10 times compared to the transformant in which only UGT72E3/2 gene is over-expressed, thus indicating an excellent effect (FIG. 12).

Figure 14:
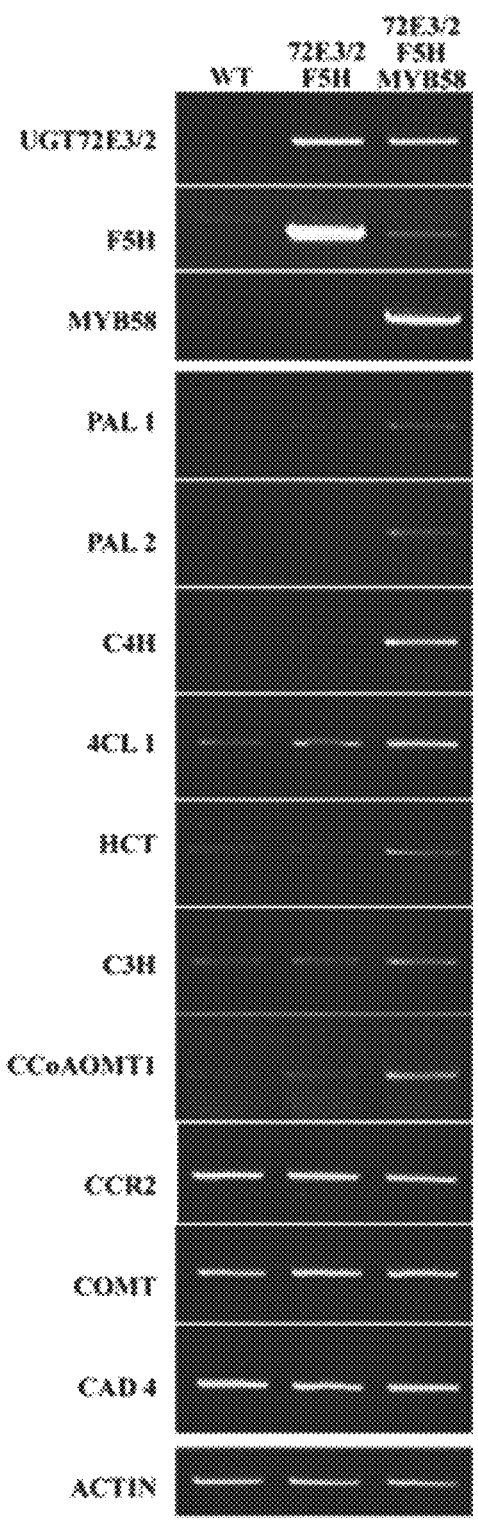
FIG. 14 is a drawing illustrating the expression amount of various genes involved with the synthesis pathway for phenylpropanoid in the transgenic *Arabidopsis thaliana* which over-expresses UGT72E3/2, F5H and Myb58 genes, the transgenic *Arabidopsis thaliana* which over-expresses UGT72E3/2 and F5H genes, and the wild type *Arabidopsis thaliana* as determined by RT-PCR. As a control group, Actin 2 gene was used.

The results of having efficient production of syringin in the leaves based on the synergistic effect among three genes that are related to syringin production, i.e., UGT72E3/2, F5H, and Myb58 genes, are in match with the results of the analysis conducted at gene level. By enhancing the expression of various genes relating to the synthesis pathway of phenylpropanoid by over-expression of Myb58 and separately over-expressing UGT72E3/2 and F5H genes that are not regulated by Myb58, the syringin production amount is remarkably increased in the leaves of the transformant (FIG. 14). Further, it was shown that the syringin production amount in the leaves of the transformant is increased by 2 times or more compared to the production amount in the roots. Thus, it was confirmed that, as a synergistic effect caused by over-expression of UGT72E3/2, F5H and Myb58 genes, the syringin production is most ideally reduced by 2 times or so in the roots while it is significantly increased in the leaves. Accordingly, a transgenic plant capable of producing syringin in a large amount was established with the aforementioned method.

The invention claimed is:

1. Recombinant glycosyl transferase UGT72E3/2 protein consisting of the amino acid sequence of SEQ ID NO: 2.

2. A gene encoding the UGT72E3/2 protein of claim 1.

3. A recombinant vector comprising the gene encoding the UGT72E3/2 protein of claim 2.

4. A host cell transformed with the recombinant vector of claim 3.

5. The host cell according to claim 4, characterized in that it is a plant cell.

6. A method of increasing syringin synthesis in a plant compared to the wild type, comprising transforming a plant cell with the recombinant vector of claim 3 to over-express the UGT72E3/2 gene.

7. A transgenic plant with increased syringin production compared to the wild type, in which the plant is transformed with a recombinant vector comprising the gene of claim 2.

8. A transgenic plant with increased syringin production compared to the wild type, in which the plant is transformed with a recombinant vector comprising the gene of claim 2 and a recombinant vector comprising the gene encoding the F5H (furulate 5-hydroxylase) protein which consists of the amino acid sequence of SEQ ID NO: 4.

9. A transgenic plant with increased syringin production compared to the wild type, in which the plant is transformed with a recombinant vector comprising the gene of claim 2, a recombinant vector comprising the gene encoding the F5H (furulate 5-hydroxylase) protein which consists of the amino acid sequence of SEQ ID NO: 4, and a recombinant vector comprising the gene encoding the Myb58 protein which consists of the amino acid sequence of SEQ ID NO: 6.

10. A transgenic plant with increased syringin production compared to the wild type, in which the plant is transformed with a recombinant vector comprising the gene of claim 2, a recombinant vector comprising the gene encoding the F5H (furulate 5-hydroxylase) protein which consists of the amino acid sequence of SEQ ID NO: 4, and a recombinant vector comprising the gene encoding the Myb63 protein which consists of the amino acid sequence of SEQ ID NO: 8.

11. A transgenic plant with increased syringin production compared to the wild type, in which the plant is transformed with a recombinant vector comprising the gene of claim 2 and a recombinant vector comprising the gene encoding the CHS (chalcone synthase) protein which consists of the amino acid sequence of SEQ ID NO: 10.

12. A method for producing a transgenic plant with increased syringin synthesis compared to the wild type, comprising:
    (a) transforming a plant cell with a recombinant vector comprising the gene of claim 2; and
    (b) regenerating a plant from the transgenic plant cell of the step (a).

13. A method for producing a transgenic plant with increased syringin production compared to the wild type, comprising:
    (a) producing a transgenic plant over-expressing the UGT72E3/2 protein by transforming a plant with a recombinant vector comprising the gene of claim 2;
    (b) producing a transgenic plant over-expressing the F5H (furulate 5-hydroxylase) protein by transforming a plant with a recombinant vector comprising the gene encoding F5H protein which consists of an amino acid sequence of SEQ ID NO: 4; and
    (c) cross-breeding the transgenic plant over-expressing the UGT72E3/2 protein of the step (a) and the transgenic plant over-expressing the F5H protein of the step (b) and selecting a transgenic plant which over-expresses simultaneously the UGT72E3/2 protein and F5H protein.

14. A method for producing a transgenic plant with increased syringin production compared to the wild type, comprising:
    (a) producing a transgenic plant over-expressing the UGT72E3/2 protein by transforming a plant with a recombinant vector comprising the gene of claim 2;
    (b) producing a transgenic plant over-expressing the F5H (furulate 5-hydroxylase) protein by transforming a plant with a recombinant vector comprising the gene encoding F5H protein which consists of an amino acid sequence of SEQ ID NO: 4;
    (c) cross-breeding the transgenic plant over-expressing the UGT72E3/2 protein of the step (a) and the transgenic plant over-expressing the F5H protein of the step (b) and selecting a transgenic plant which over-expresses simultaneously the UGT72E3/2 protein and F5H protein;
    (d) producing a transgenic plant over-expressing the Myb58 protein by transforming a plant with a recombinant vector comprising the gene encoding Myb58 protein which consists of an amino acid sequence of SEQ ID NO: 6; and
    (e) cross-breeding the transgenic plant over-expressing simultaneously the UGT72E3/2 protein and F5H protein of the step (c) and the transgenic plant over-expressing the Myb 58 protein of the step (d) and selecting a transgenic plant which over-expresses simultaneously the UGT72E3/2 protein, F5H protein, and Myb58 protein.

15. A method for producing a transgenic plant with increased syringin production compared to the wild type, comprising:
    (a) producing a transgenic plant over-expressing the UGT72E3/2 protein by transforming a plant with a recombinant vector comprising the gene of claim 2;
    (b) producing a transgenic plant over-expressing the F5H (furulate 5-hydroxylase) protein by transforming a plant with a recombinant vector comprising the gene encoding F5H protein which consists of an amino acid sequence of SEQ ID NO: 4;
    (c) cross-breeding the transgenic plant over-expressing the UGT72E3/2 protein of the step (a) and the transgenic plant over-expressing the F5H protein of the step (b) and selecting a transgenic plant which over-expresses simultaneously the UGT72E3/2 protein and F5H protein;
    (d) producing a transgenic plant over-expressing the Myb63 protein by transforming a plant with a recombinant vector comprising the gene encoding Myb63 protein which consists of an amino acid sequence of SEQ ID NO: 8; and
    (e) cross-breeding the transgenic plant over-expressing simultaneously the UGT72E3/2 protein and F5H protein of the step (c) and the transgenic plant over-expressing the Myb63 protein of the step (d) and selecting a transgenic plant which over-expresses simultaneously the UGT72E3/2 protein, F5H protein, and Myb63 protein.

16. A method for producing a transgenic plant with increased syringin production compared to the wild type, comprising:
    (a) producing a transgenic plant over-expressing the UGT72E3/2 protein by transforming a plant with a recombinant vector comprising the gene of claim 2;
    (b) producing a plant in which the gene encoding the CHS (chalcone synthase) protein consisting of an amino acid sequence of SEQ ID NO: 10 is knocked out; and
    (c) cross-breeding the transgenic plant over-expressing the UGT72E3/2 protein of the step (a) and the plant with knocked-out CHS protein-coding gene of the step (b) and selecting a transgenic plant which over-expresses the UGT72E3/2 protein and suppresses expression of the CHS protein.

17. A transgenic plant with increased syringin production compared to the wild type, which is produced by the method described in claim 12.

18. The plant according to claim 17, in which the plant is a dicot plant.

19. A seed of the transgenic plant of claim 17, wherein the seed comprises the recombinant vector.

20. A composition for increasing syringin synthesis in a plant comprising, a recombinant vector comprising the gene consisting of the nucleotide sequence of SEQ ID NO: 1 which encodes the UGT72E3/2 protein.

* * * * *